US012115354B2

(12) United States Patent
Biegelsen et al.

(10) Patent No.: US 12,115,354 B2
(45) Date of Patent: *Oct. 15, 2024

(54) ALIGNMENT OF ELONGATED PARTICLES IN A PARTICLE DELIVERY DEVICE

(71) Applicant: Palo Alto Research Center Incorporated, Palo Alto, CA (US)

(72) Inventors: David K. Biegelsen, Portola Valley, CA (US); Eugene M. Chow, Palo Alto, CA (US); Armin R. Volkel, Mountain View, CA (US); Ashish Pattekar, Cupertino, CA (US); Mandana Veiseh, Piedmont, CA (US)

(73) Assignee: Xerox Corporation, Norwalk, CT (US)

( * ) Notice: Subject to any disclaimer, the term of this patent is extended or adjusted under 35 U.S.C. 154(b) by 540 days.

This patent is subject to a terminal disclaimer.

(21) Appl. No.: 17/391,446

(22) Filed: Aug. 2, 2021

(65) Prior Publication Data
US 2021/0353865 A1   Nov. 18, 2021

Related U.S. Application Data

(63) Continuation of application No. 16/582,217, filed on Sep. 25, 2019, now Pat. No. 11,077,251, which is a
(Continued)

(51) Int. Cl.
*A61M 5/30*   (2006.01)
*A61M 5/20*   (2006.01)
*A61M 37/00*  (2006.01)

(52) U.S. Cl.
CPC ......... *A61M 5/3015* (2013.01); *A61M 5/2046* (2013.01); *A61M 5/2053* (2013.01);
(Continued)

(58) Field of Classification Search
CPC ........ A61M 2037/0007; A61M 5/3015; A61M 2202/064; A61M 37/00; A61M 37/0076;
(Continued)

(56) References Cited

U.S. PATENT DOCUMENTS 4,326,524 A   4/1982   Drake, Jr. et al.
4,734,090 A * 3/1988   Sibalis ................ A61N 1/0448
                                                                604/20
(Continued)

FOREIGN PATENT DOCUMENTS

EP         0254166      10/1989

OTHER PUBLICATIONS

Antov et al., "Electroendocytosis: Exposure of Cells to Pulsed Low Electric Fields Enhances Adsorption and Uptake of Macromolecules", Biophysical Journal, vol. 88, Mar. 2005, pp. 2206-2223.
Banga et al., "Assessing the potential of skin electroporation for the delivery of protein- and gene-based drugs", Trands Biotechnol., vol. 10, Oct. 1998, pp. 408-412.
Browning, "Enhancing transdermal delivery of drug-infused particles using electrostatic pulse", Boston University 2013, 68 pages.
Dubey, "Laser Microporation for the Delivery of Drugs into and Across the Skin", Bulletin of Pharmaceutical Research 2012; 2(3), pp. 118-123.
(Continued)

*Primary Examiner* — Jason E Flick
(74) *Attorney, Agent, or Firm* — Mueting Raasch Group

(57) ABSTRACT

A device for delivery of particles into biological tissue includes at least one conduit and a propellant source fluidically coupled to the conduit and configured to deliver a propellant into the conduit. A particle source is configured to release elongated particles into the conduit, the elongated particles having a width, w, a length, l>w. The propellant source and the conduit are configured to propel the elongated particles in a collimated particle stream toward the biological tissue. An alignment mechanism is configured to align a longitudinal axis of the elongated particles to be substantially parallel to a direction of the particle stream in an alignment region of the conduit. The aligned elongated particles are ejected from the conduit and impact the biological tissue.

20 Claims, 28 Drawing Sheets

Related U.S. Application Data continuation of application No. 14/617,415, filed on Feb. 9, 2015, now Pat. No. 10,449,297.

(52) U.S. Cl.
CPC .............. *A61M 2037/0007* (2013.01); *A61M 2202/064* (2013.01)

(58) Field of Classification Search
CPC ............ A61M 37/0092; A61M 5/2046; A61M 5/2053; A61N 2005/067; A61N 2/002; A61N 5/062
See application file for complete search history.

(56) References Cited

U.S. PATENT DOCUMENTS

| | | | | |
|---|---|---|---|---|
| 5,584,807 | A | * | 12/1996 | McCabe ................ C12M 35/00 604/59 |
| 5,725,497 | A | | 3/1998 | Woodruff et al. |
| 5,899,880 | A | | 5/1999 | Bellhouse et al. |
| 6,207,400 | B1 | | 3/2001 | Kwon |
| 6,372,045 | B1 | | 4/2002 | McCabe |
| 7,727,223 | B2 | | 6/2010 | Potter et al. |
| 8,388,569 | B2 | | 3/2013 | Uhland et al. |
| 2007/0264349 | A1 | | 11/2007 | Lee et al. |
| 2010/0303916 | A1 | * | 12/2010 | Finlay .................. A61K 9/0078 604/93.01 |
| 2010/0311671 | A1 | | 12/2010 | Johnson et al. |
| 2012/0271221 | A1 | * | 10/2012 | Uhland ............... A61M 5/3007 604/24 |

OTHER PUBLICATIONS

Gandhi et al., "Transdermal drug delivery—A review", Int. J. Res. Pharm. Sci., 3(3), 2012, pp. 379-388.

Katz et al., "Alignment and self-assembly of elongated micronsize rods in several flow fields", Journal of Applied Physics, vol. 100, 2006, p. 034313-1-034313-12.

Liu, "Intradermal Needle-Free Powdered Drug Injection", Jun. 2012, 80 pages.

Paudel et al., "Challenges and opportunities in dermal/transdermal delivery", Ther Deliv., Jul. 2010; 1(1), pp. 109-131.

Raphael et al., "Elongate microparticles for enhanced drug delivery to ex vivo and in vivo pig skin", J. Control Release, vol. 172 (1) Nov. 28, 2013, pp. 96-104.

Scheiblhofer et al., "Laser microporation of the skin: prospects for painless application of protective and therapeutic vaccines", Informa healthcare, 2013, pp. 761-773.

Schmidt, "Dynamics of Optically Trapped Microparticles in Hollow-Core Photonic Crystal Fibers", Dissertation Jun. 13, 2014, 144 pages.

Stevenson et al., "Light forces the pace: optical manipulation for biophotonics", Journal of Biomedical Optics, vol. 15 (4), Jul./Aug. 2010, 041503-1-041503-21.

Svarovsky et al., "Self-Assembled Micronanoplexes for Improved Biolistic Delivery of Nucleic Acids", Molecular Pharmaceutics, Sep. 14, 2009, 7 pages.

Uchechi et al., "Nanoparticles for Dermal and Transdermal Drug Delivery", Chapter 6, 2014, pp. 193-235.

\* cited by examiner

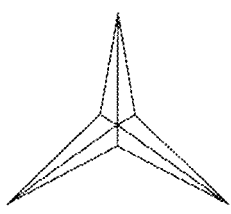 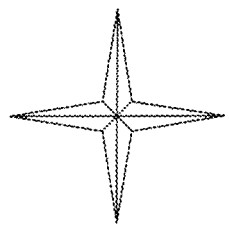 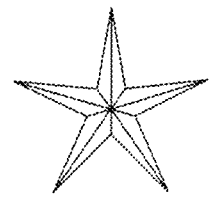
FIG. 9A    FIG. 9B    FIG. 9C
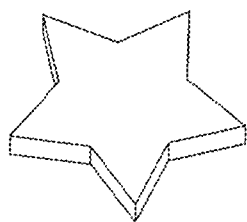 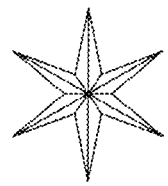 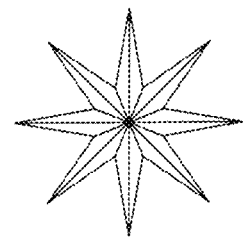
FIG. 9D    FIG. 9E    FIG. 9F

ALIGNMENT OF ELONGATED PARTICLES IN A PARTICLE DELIVERY DEVICE

RELATED APPLICATIONS

This application is a continuation of U.S. Ser. No. 16/582,217, filed Sep. 25, 2019, which is a continuation of U.S. Ser. No. 14/617,415, filed Feb. 9, 2015, now U.S. Pat. No. 10,449,297, which are incorporated herein by reference in their entireties.

TECHNICAL FIELD

This disclosure generally involves approaches for delivering particles into biological tissue and to systems and methods related to such approaches.

BACKGROUND

Particles that can be accelerated to penetrate the skin can have a very low active payload when a relatively light functional material, such as a drug, ink, cosmetics, etc., needs to be coated on dense, carrier particles such as gold. Solid particles of the functional material most efficiently carry the functional material in higher doses. However, the relatively light particle of functional material may not have enough momentum to be delivered into biological tissue at sufficient depth to reach target cells. Advanced gene therapies, such as DNA/RNA based vaccines, gene based cancer tumor therapies, and genetic pharmacology need new delivery methods to penetrate cells.

SUMMARY

A device for delivery of particles into biological tissue includes at least one conduit and a propellant source fluidically coupled to the conduit and configured to deliver a propellant into the conduit. A particle source is configured to release elongated particles into the conduit, the elongated particles having a width, w, a length, l>w. The propellant source and the conduit are configured to propel the elongated particles in a collimated particle stream toward the biological tissue. An alignment mechanism is configured to align a longitudinal axis of the elongated particles to be substantially parallel to a direction of the particle stream in an alignment region of the conduit. The aligned elongated particles are ejected from the conduit and impact the biological tissue.

According to some implementations, the alignment mechanism comprises an aerodynamic alignment mechanism that includes a source of sheath fluid and one more ports in the conduit configured to allow entry of the sheath fluid into the conduit in one or more sheath streams adjacent to the particle stream. The one or more sheath streams are configured to align the longitudinal axis of the elongated particles along the direction of the particle stream in the alignment region.

According to some implementations the elongated particles are electrically charged and the alignment mechanism comprises an electrostatic alignment mechanism comprising one or more charged plates arranged proximate to the conduit.

In some implementations the elongated particles are magnetic and the alignment mechanism comprises a magnetic field generator that generates a magnetic field within the conduit.

The elongated particles may have various features that enhance alignment, such as at least one pointed tip and/or one or more fins. The fins can be configured to break off or fold back when the elongated particles penetrate the biological tissue.

In some implementations the elongated particles are solid particles of a functional material that interacts with the biological tissue. In some cases the elongated particles include two or more types of material such as at least a first material and a second material. The second material may be a functional material that interacts with the biological tissue and the first material may be a biologically inert material that has higher density than the second material. In some implementations, the volume of the second material in the elongated particle is greater than the volume of the first material. The elongated particles may comprise a drug, a cosmetic, a biologically nourishing material, or a marking material.

According to some embodiments, the particle delivery device includes a particle accelerator downstream from the alignment mechanism. The particle accelerator is configured to accelerate the elongated particles toward the biological tissue.

Some implementations of the particle delivery device further include an additional particle source configured to release additional particles into the particle stream. The elongated particles comprise a functional material that interacts with the biological tissue and the additional particles have a higher density than a density of the elongated particles. In some implementations, the elongated particles are electrostatically charged and the additional particles are oppositely electrostatically charged from the elongated particles. Due to their opposite charges, the elongated particles and the additional particles form particle agglomerations as the particles are transported in the particle stream.

Some embodiments involve a method for delivery of particles into biological tissue. Elongated particles having a width, w, a length, l>w, and an aspect ratio, l/w, are released into a conduit and are propelled in a collimated particle stream in the conduit. The longitudinal axis of the elongated particles are aligned to be substantially parallel to a direction of the collimated particle stream. The aligned elongated particles are ejected from the conduit toward the biological tissue. Aligning the longitudinal axis of elongated particles may comprise introducing a sheath fluid into the conduit in one or more sheath streams adjacent to the collimated particle stream. The one or more sheath streams operate to align the longitudinal axis of the elongated particles to be substantially parallel to the direction of the particle stream in an alignment region.

In some implementations the elongated particles are electrically charged and aligning the elongated particles comprises electrostatically aligning the elongated particles.

In other implementations the elongated particles are magnetic and aligning the elongated particles comprises magnetically aligning the elongated particles.

The aligned elongated particles may be accelerated toward the biological tissue using an electrostatic particle accelerator. The each of the elongated particles may comprise one or more of increased density at one end of the elongated particle and an aerodynamic drag feature.

The method may include pre or post treating the biological tissue before or after ejecting the aligned elongated particles from the conduit toward the biological tissue. The pre or post treating can comprise at least one of a laser treatment, a magnetic treatment, an electromagnetic treatment, an ultrasonic treatment and a chemical treatment.

Some embodiments involve a device for delivery of particles into biological tissue that includes at least one conduit and a propellant source fluidically coupled to the conduit and configured to deliver a propellant into the conduit. A particle source is configured to release elongated particles into the conduit, the elongated particles having a width, w, a length, l>w. The propellant source and the conduit are configured to accelerate the elongated particles in a collimated particle stream toward the biological tissue. Acceleration of the particles by the propellant aligns a longitudinal axis of the elongated particles to be substantially parallel to a direction of the particle stream. Each of the elongated particle may include at least one of a feature that provides enhanced aerodynamic drag and increased density at one end of the particle.

BRIEF DESCRIPTION OF THE DRAWINGS

FIGS. 9A through 9G show exemplary configurations of two dimensional and dimensional particles comprising of a core and plurality of elongations distributed on the surface of the core;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
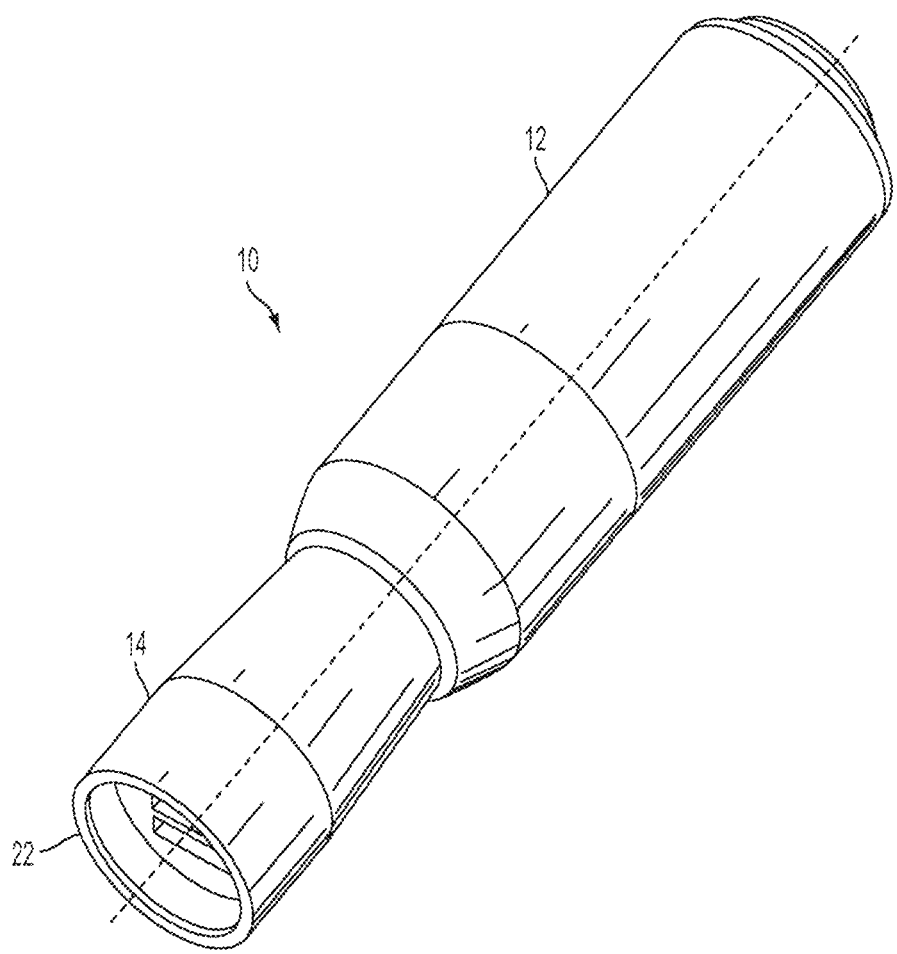
FIG. 1 is a perspective view, illustrating a particle delivery device in accordance with one or more embodiments of the present disclosure.

Embodiments described herein are directed to systems and methods for delivering particles into biological tissue. According to the approaches described herein, one or more collimating conduits are disposed within a housing with a propellant, e.g., a pressurized gas, fluidically coupled to the one or more collimating conduits. The conduits include openings that allow introduction of particles into the conduit. The propellant source and the conduits are arranged so that as the particles are introduced, they are entrained by the gas from the propellant source and are propelled along the conduit in a particle flow stream.

As previously discussed, solid particles of functional material are needed to efficiently carry the functional material into tissue at higher doses. However particles of functional material may not have enough momentum to be delivered into biological tissue at sufficient depth to reach target cells. According to some implementations discussed below, particles that are heavier and/or denser than the lighter/lower density functional particles are ejected from the conduits, forming micropores in the biological tissue, at least temporarily. The heavier/denser particles may have a density greater than about 10 g/cm$^3$, a volume greater than 0.07 μm$^3$, and weight range of 0.5 pg to 100 mg. When penetrating the tissue, the heavier/denser particles may present an average cross sectional area substantially perpendicular to the tissue surface of greater than 0.2 μm$^2$. The lighter/lower density second particles are ejected from the conduits, in some cases subsequently or substantially simultaneously with ejection of the heavier first particles. The heavier/denser particles may have a density more than about three times the density of the lighter/less dense particles. The lighter/less dense particles may have a density less than about 10 g/cm$^3$ with diameter range of 50 nm to 1 mm. When penetrating the tissue, the lighter/lower density functional particles may present an average cross sectional area perpendicular to the tissue surface that is equal to or less than that of the heavier particles. For example, the average presenting cross sectional area of the lighter/lower density particles may be a fraction (½, ¼, etc.) of that of the heavier particles. In some scenarios, the heavier/denser first particles penetrate the biological tissue to create micropores that increase porosity of the biological tissues. The lighter/less dense second particles penetrate the porous biological tissue previously formed by the first particles. If the first particles follow the second particles, the second particles may be driven further into the tissue. This approach allows the lighter/lower density second particles to penetrate the skin via the micropores formed by the first particles to reach target cells.

According to some implementations, the first particles and second particles are initially collimated in the conduit by the conduit walls and may be subsequently focused in the conduit by a focusing mechanism. Particle collimation followed by focusing achieves enhanced spatial correlation between the first and second particles as they emerge from the device, which in turn leads to more effective delivery of functional material. Focusing occurs in a focus region of the conduits which may be located near the conduit outlets. The first and second particles may be focused alone or together such that the largest cross sectional diameter of the focused particle stream in the focus region is less than the largest inner cross sectional diameter of the conduit in the focus region. In some cases, the largest cross sectional diameter of the focused particle stream in the focus region is equal or greater than the presenting cross sectional diameter of the first particles, wherein the presenting cross section is the cross section of the particle that is substantially perpendicular to the direction of the flow stream.

In some implementations, the device includes a tissue-interfacing surface located at one end of the housing near the conduit outlets that provides an interface with the surface of biological tissue. The collimated and focused particle stream emerges from the outlet substantially perpendicular to the biological tissue surface and can maintain a beam diameter of less than 10 μm or equal to the presenting cross sectional diameter of the first particles over a length of about 1 cm or more between the outlet of the conduit and the tissue surface. In the unconstrained space between the conduit outlet and the tissue surface, the particle stream width may increase by less than about 10% of its width at the outlet.

According to some implementations, the particles, e.g., the first and/or second particles or other particles, are elongated particles that have a width (w) and a length (l), wherein l>w. An alignment mechanism may be used to rotationally align the elongated particles so that the major axis (also referred to as the length axis) of the particles is substantially parallel with the direction of the particle flow stream in the conduit. The particles may have a relatively high aspect ratio, e.g., l/w is in the range of 10 to 1000 and may include features, such as sharpened tips, fins, anisotropic weighting, structured surfaces and the like, that enhance alignment, tissue penetration, and surface area available for carrying a functional material. The particles emerge from the outlets of the conduits in the aligned orientation in a collimated particle stream and impinge on the tissue surface. According to some aspects, the aligned particles may also be focused into a narrower cross sectional area prior to ejection from the device.

Devices, methods, and systems are provided for producing high velocity, e.g., supersonic, particle streams of collimated, focused and/or aligned particles that maintain a beam diameter less than 50 μm, or less than or equal to about 20 μm, or equal to or greater than the presenting cross sectional diameter of the first particles, less than the larger inner diameter of conduit. In some implementations, the particle stream width increases by less than 10% over a length of about 1 cm or more in the space between the outlet of the conduit and the tissue surface. When the particles are focused in addition to being collimated, the beam diameter increase of less than 5% may be maintained over an unconstrained 1 cm length. The approaches described herein may reduce or eliminate recoil/splashing, pain, and bruising associated with other needleless injection techniques. Such devices, methods, and systems can also provide increased control and reliability of drug delivery and reduce the operational skill required to perform needleless drug injection. This, in turn, promotes more precise and accurate drug dosing.

The devices, systems, and methods described herein may be used for targeted delivery of therapeutic, diagnostic, cosmetics, or other substances into or through a variety of types of tissues or biological barriers, including suitable cells, tissues, or organs, including the skin or parts thereof, mucosal tissues, vascular tissues, lymphatic tissues, and the like. The target cells or tissues may be in animals, mammals, humans, plants, insects, or other organisms. For example, a drug or other substance may be delivered through the stratum corneum, and into underlying dermal or epidermal tissues or cells.

According to some embodiments, a particle delivery device includes a propellant source, which may be a source that contains or produces a pressurized gas. The delivery device also includes one or more collimators, each collimator comprising one or more conduits that are fluidly connected with the fluid source. Each of the conduits is configured to form a collimated particle stream comprising particles entrained in and propelled by the gas. According to some embodiments, the particle delivery device may further include a skin interfacing surface that is adapted to mate with the skin (or other tissue surface) and align the ejector with the skin such that the plurality of collimated particle streams penetrate the skin in a direction substantially perpendicular to the skin. The skin interfacing surface is disposed on a skin interfacing unit located downstream of the conduit outlet. In some embodiments, described below in connection with FIG. 16D, the particle delivery system may include a mechanism configured to decelerate and/or to reduce an amount of the sheath fluid as the sheath fluid approaches the skin surface. The mechanism may be part of the tissue interfacing portion of the particle delivery device and/or may be located near the conduit outlet. For example, in some embodiments, the mechanism can be located after the focused region and before interfacing with tissue. The mechanism may redirect the propellant sheath stream from the high speed stream of particles such that at least a portion of the propellant sheath stream does not impinge on the biological tissue or impinges on the biological tissue at an oblique (non-perpendicular) angle.

The delivery device may include one or more reservoirs of functional and non-functional material, e.g., a reservoir containing a drug in solid particle or liquid form that is fluidically coupled to at least one conduit of the collimators via a port between the inlet end and the outlet end of the conduit. The port is fluidly connected (or is operable to become fluidly connected) with the reservoir, and the inlet end of each of the conduit is fluidly connected (or is operable to become fluidly connected) with the gas source.

In certain embodiments, the delivery device is configured to produce focused, collimated gas streams having a sufficient velocity to penetrate human stratum corneum. For example, the delivery device may be configured to produce collimated gas streams having a velocity of about 30 to about 1500 m/s. In certain embodiments, each of the collimated gas streams may have a diameter of about 1 µm to about 1000 µm at a distance of about 0.5 mm to 10 mm from the outlet of the collimator.

The collimated and focused particle stream emerges from the outlet substantially perpendicular to the biological tissue surface and can maintain a beam diameter of less than 10 µm or equal to the presenting cross sectional diameter of the first particles over a length of about 1 cm or more between the outlet of the conduit and the tissue surface. In the unconstrained space between the conduit outlet and the tissue surface, the particle stream width may increase by less than about 10% of its width at the outlet.

Effective collimation may be achieved by delivering a propellant into a conduit and controllably introducing or metering the particles into the conduit. The particles may then be introduced into the gas stream from one or more inlet ports. The propellant may enter the channel at a high velocity. Alternatively, the propellant may be introduced into the channel at a high pressure, and the conduit may include a constriction (e.g., de Laval or other converging/diverging type nozzle) for converting the high pressure of the propellant to high velocity. In such a case, the propellant is introduced at a port located at a proximal end of the conduit (i.e., near the converging region), and the material ports are provided near the distal end of the channel (at or further downstream of a region defined as the diverging region), allowing for introduction of material into the propellant stream. It has been demonstrated that a propellant and the material flow pattern can remain relatively collimated for a distance of up to 10 millimeters. For example, the stream does not deviate by more than about 20 percent, and preferably by not more than about 10 percent, from the width of the exit orifice for a distance of at least 4 times the exit orifice width.

Figure 4:
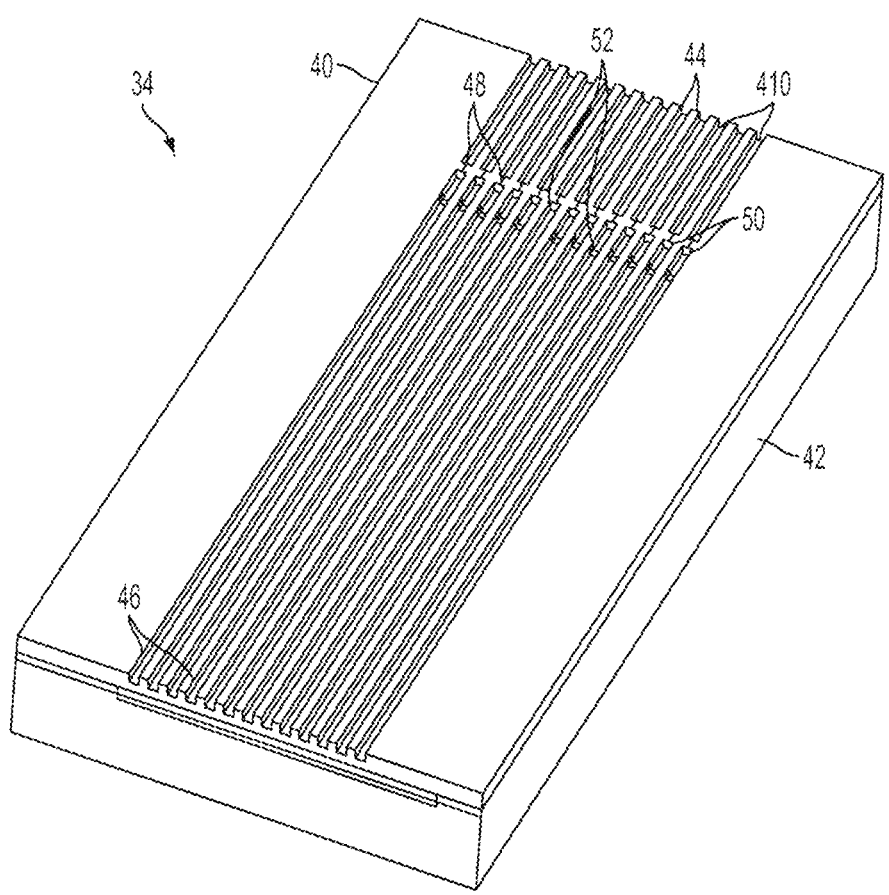
FIG. 4 is a detail view, illustrating an ejector for a particle delivery device in accordance with one or more embodiments of the present disclosure.

In certain embodiments, the collimator may include a plurality of conduits. Each conduit has inlet and an outlet, as shown in FIG. 4. Each of the conduits may have a venturi, converging/diverging type nozzle, located between the inlet end and the outlet end. In certain embodiments, each conduit has an expansion neck region which expands the gas stream downstream of the venturi neck. For example, an expansion neck region may be provided at the exit of the venturi.

In some embodiments, the particle delivery device releases a particle from a particle source into the gas streams such that the particles becomes entrained in each gas stream and are transported into the skin in a direction substantially perpendicular to the skin. For example, each of the conduits may have a port that provides an opening between the inlet and outlet of the conduit, that is fluidly connected with the particle source. In certain embodiments, the port is downstream of the venturi. In some embodiments, the delivery device includes a rupturable membrane between the particle source and the collimator. For example, the rupturable membrane may seal the port until the membrane is ruptured. Rupture of the rupturable membrane may be controlled by the operator of the device.

When the particle port is placed downstream of the venturi or downstream of the location at which the high velocity stream of gas is established, the particles may be pushed into the high velocity gas stream by a pressure differential (e.g., Bernoulli's force). For example, based on Bernoulli's equation, if particles are contained in an open reservoir adjacent to a high velocity gas stream of 750 m/s, a pressure difference of about 2.2 atm is generated and pushes the particles into the gas stream.

The delivery device may include a standoff between the collimator and the skin interfacing surface such that a gap is provided between the outlets of the collimator and the skin when the skin interfacing surface is placed against the tissue. For example, the standoff may create a gap of about 0.5 to about 10 mm between the outlets of the collimator and the tissue surface. The standoff further allows the fluid stream to be diverted from the tissue and exhaust laterally from the stream. The entrained particles, having much higher momentum, continue their flight towards the tissue at substantially normal incidence.

In some embodiments, the collimator and particle source are provided in the form of a removable cartridge. The drug delivery device may include one or more cartridge receivers for receiving one or more removable cartridges. The cartridge may be inserted into the receiver for delivering particles, e.g., drug particles contained in the cartridge into a patient's skin. The cartridge, which may be depleted of drug, may thereafter be removed and replaced. In some embodiments, the drug delivery device includes a plurality of cartridge receivers for receiving multiple cartridges. In certain embodiments, each cartridge may contain an amount of a drug suitable for an individual dosage.

According to some aspects, the delivery device is configured to deliver first and second particles, wherein the first particles are heavier and/or have higher density than the second particles. The delivery device includes a collimator as discussed above and may include a focusing mechanism configured to focus the collimated particle stream to enhance the spatial correlation of the first and second particles in the particle stream. The heavier/denser first particles are used to precondition the tissue in a geometric pattern, such as a spot array, to enhance subsequent delivery via the lighter/lower density particle. For example, the heavy/denser first particles may be inert and/or decomposable by the tissue and the lighter/lower density particles may comprise a functional material such as a drug. The heavier/denser particles can be accelerated through an array of microjets to generate temporary holes in cell walls to increase permeability of cell walls to drug and/or the tissue. Lighter, lower density, solid particles can be subsequently delivered through the same array of microjets so that the lighter/lower density particles impinge the skin in the same regions which have enhanced permeability, enabling solid drugs and/or other functional agents to be delivered intracellularly and at a specified depth. The diameter of the particle beam is focused to be small enough so that there is an enhanced and high likelihood of overlap between the landing site of the preconditioning heavier/denser particle and the landing site of the lighter/lower density, functional particle.

In some embodiments, the particles delivered by the device may be elongated, high aspect ratio particles. The elongated particles may be lighter, solid particles of a functional agent, e.g., a drug, and/or may be heavier/denser inert particles, and/or may comprise a combination inert heavy/dense material and lighter functional material. The delivery device may include an alignment mechanism configured to align elongated particles in the particle stream such that their length axis is substantially parallel to the conduit axis and along the movement direction of the particle stream.

Figure 2:
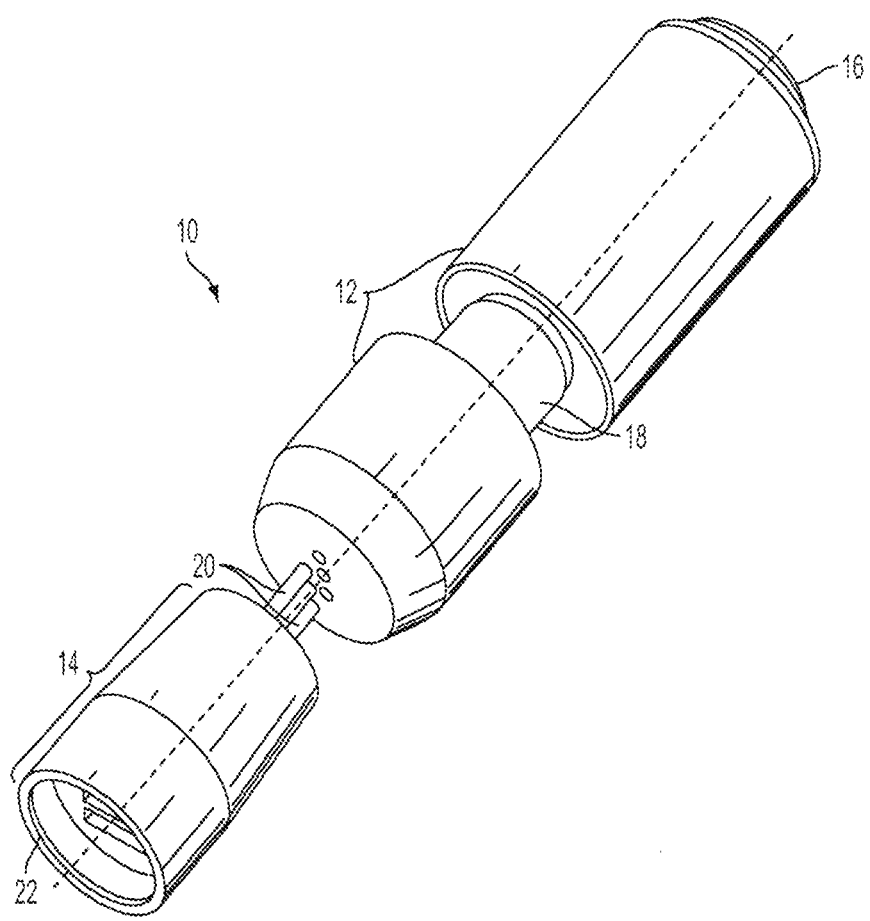
FIG. 2 is an exploded perspective view, illustrating a particle delivery device in accordance with one or more embodiments of the present disclosure.
Figure 3:
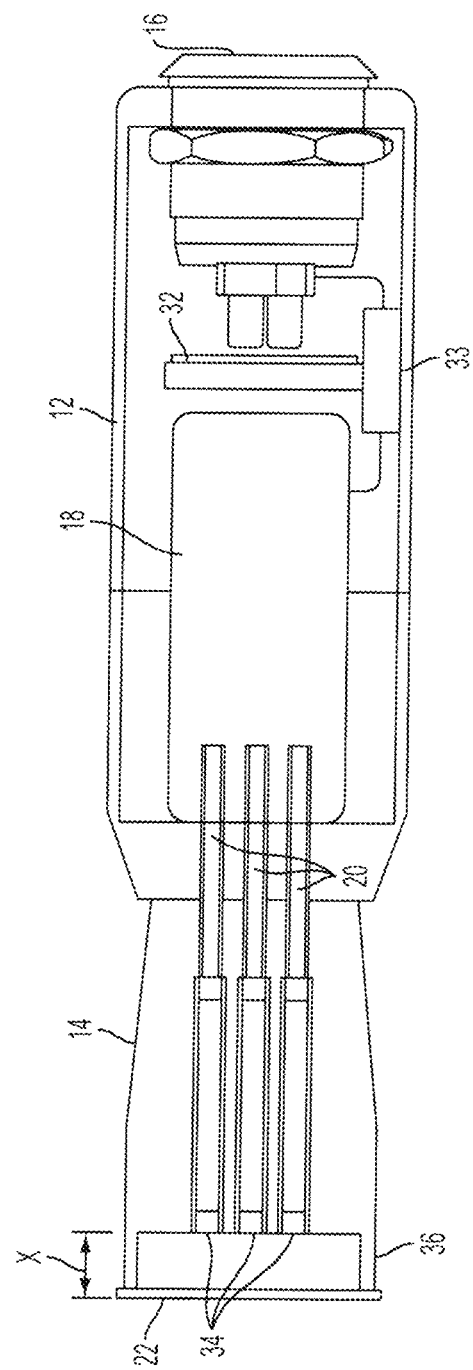
FIG. 3 is a section view, illustrating a particle delivery device in accordance with one or more embodiments of the present disclosure.

An exemplary embodiment of a particle delivery device 10 is illustrated in FIGS. 1-3. Although the delivery device is illustrated herein as a hand held particle injector, it will be appreciated that the particle delivery device may alternatively attached to or incorporated into various other devices, such as catheter, a probe, needles or a surgical device for example. The particle delivery device 10 includes a gas source housing 12 and a cartridge housing 14. The gas source housing 12 may be dimensioned to fit comfortably in a hand when the fingers are wrapped around the cylindrical sidewall of the gas source housing 12. The particle ejector housing 14 is located at one end of the drug delivery device 10. As illustrated in FIG. 2, the ejector housing 14 may be located at the end of the delivery device 10 opposite a push switch 16. Although the push switch 16 is illustrated at one end of the delivery device 10, the push switch 16 can also be located elsewhere on the device, such as on the cylindrical sidewall of the gas source housing 12. The cartridge housing 14 includes at one end a tissue interfacing surface 22. The tissue interfacing surface 22 may be a generally planar surface that is adapted to align the collimator in a substantially perpendicular direction to the tissue surface.

As illustrated in FIG. 3, the gas source housing 12 also surrounds a gas source 18, which contains or generates a pressurized gas. In some embodiments, the gas source 18 may be or comprise a replaceable gas container or cartridge that holds the gas and which can be placed within the gas source housing 12. The gas in the replaceable container may be pre-pressurized or may be pressurized after placement in the gas source housing 12. For example, gas pressures greater than or equal to about 0.2 MPa would be sufficient to entrain and drive the particles from the delivery device. The pressurized gas may be various gases, including, but not limited to air, carbon dioxide, nitrogen, helium, or oxygen. In some embodiments, gas is generated on-board. For example, gas may be generated on-board by a chemical or electro-chemical reaction. One example of such a system includes an electrochemical cell that breaks down water into hydrogen gas ($H_2$) and oxygen gas ($O_2$). The water source could be in liquid form or stored in a hydrogel on-board the device. Another example is a system that relies on phase transformation, such as boiling of water to generate steam. Still other examples include systems that utilizes a chemical reaction or decomposition, for instance, sodium azide decomposition into sodium and nitrogen gas ($N_2$) or the reaction of calcium carbonate with an acid to yield carbon dioxide gas ($CO_2$). In some embodiments, the gas is provided in a pressurized vessel and is delivered, such as through a valve, to the collimator when needed. For example, the valve may be actuated by pressing a push switch on the drug delivery device. In some embodiments, the pressure may be generated by a mechanical device, such as a pump.

In the embodiment of FIG. 3, the pressurized gas is selectively delivered to one of three ejector cartridges 34 via a corresponding gas delivery conduit 20. Gas delivery may be actuated by pressing the push switch 16. A power source 32 and a controller 33 may then selectively actuate a valve to control the flow of pressurized gas from the gas source 18 through the desired gas delivery conduit 20. For example, the controller 33 may separately simultaneously, or sequentially activate one of three control valves with each press of the push switch 16. In embodiments in which gas is generated on-board the delivery device 10, the controller 33 may also actuate the process that generates the gas.

The ejector housing 14 in the illustrated example includes three ejector receivers for receiving the three ejectors 34. The ejectors 34 may be removable and replaceable, such that the new ejectors can be inserted into the ejector receivers once the original ejectors 34 are expended. To this end, the ejector housing 14 may comprise ejector removal devices, e.g., spring-loaded push rods, to facilitate the removal of expended ejectors from the cartridge housing 14. Although slots for three ejectors 34 are illustrated in the present embodiment, it should be noted that the device could be designed to accommodate one, two, four, or any number of ejectors 34. As shown in FIG. 3, the ejector housing 14 includes a standoff 36 which provides a gap of distance x between the end of the ejectors 34 and tissue interfacing surface 22. In some embodiments, the distance x of the gap may between about 0.1 and about 5 mm.

The device may include a collimator for producing a plurality of discrete collimated gas streams. The term "collimated" as used herein refers to a stream of gas which may include solid particles, e.g., first and/or second particles as discussed above, or liquid entrained therein, that maintains a well-defined and substantially constant diameter over a desired, useful distance, including when unconstrained by a sidewall structure. For example, the collimator may provide a stream of gas and particles having a diameter of about 1 μm to about 1000 μm over an unconstrained distance (unconstrained by channel walls of the conduit) of about 0.5 mm to about 10 mm. The particle delivery device may be configured and arranged to produce gas streams having a velocity of about 30 to about 1500 m/s.

The collimated and focused particle stream emerges from the outlet substantially perpendicular to the biological tissue surface and can maintain a beam diameter of less than 10 μm or equal to the presenting cross sectional diameter of the first particles over a length of about 1 cm or more between the outlet of the conduit and the tissue surface. In the unconstrained space between the conduit outlet and the tissue surface, the particle stream width may increase by less than about 10% of its width at the outlet.

The first particles and the second particles may be propelled to different velocities. For example, the first particles maybe have a higher velocity than the velocity of the second particles to retain functional material integrity of the second particles.

An exemplary ejector 34 comprising a collimator 40 is illustrated in FIG. 4. The collimator 40 includes a plurality of conduits 410, which may be etched, cut or milled on the surface of a plate. Although the conduits 410 are illustrated as open channels in FIG. 4, it should be appreciated that the conduits 410 are bounded by a top layer when used. The top layer may be integral with the ejector 34 or it may be a surface of the ejector receiver that mates with the collimator 40 when the ejector 34 is received in the cartridge receiver. Each of the conduits 410 has an inlet 44 at one end of the ejector 34 and an outlet 46 at the other end of the ejector 34. A venturi 48 is provided in each conduit 410 between the inlet 44 and the outlet 46. Each conduit 410 includes an expanding neck region 50 downstream of each venturi 48. As the pressurized gas passes through the venturi 48, expands into the expanding neck region 50, and exits through outlet 46, well-defined, collimated gas streams are formed. The venturi 48 may be designed so as to produce an exit pressure of approximately 1 atmosphere such that the pressure inside the conduit is substantially equal to atmosphere, so as to not produce an expanding or contracting jet.

One or more ports 52 in the conduits 410 are provided downstream of the venturi 48 for releasing particles from one or more sources 42 into the gas stream where they become engrained in the flow stream. The particles delivered by the collimator 40 may include drug and/or non-drug particles into biological tissue as is described in greater detail herein.

Particles, e.g., first or second particles as discussed above, may be provided on-board the particle delivery device from one or more particle sources. In some embodiments, the particle sources comprise one or more particle reservoirs. As previously described, a particle port may be provided between each particle source and the collimator for allowing release of the particles therethrough into the conduits of the collimator.

Release of the particles may be controlled by a rupturable membrane that seals the particle port. The rupturable membrane may be ruptured by the pressure change caused by the pressurized gas being fed through the collimator. Alternatively, the rupturable membrane may be ruptured by actuation of another element. For example, the rupturable membrane may be ruptured by electrothermal ablation, mechanical puncturing (e.g., with a scepter), heating (e.g., melting the membrane), chemical reaction, or volumetric expansion of the reservoir contents.

Other release devices may be provided to control the release of the particles from the particle reservoir. For example, an electric charge or movable cover may be used to prevent the release of the particle through the drug port until such later time that release is desired and the release device is actuated.

In some embodiments, the particles may be released from a release-activatable tape. For example, the release-activatable tape may have the particles disposed on the tape. The release-activatable tape may comprise a UV-sensitive, heat-sensitive, or electrical-sensitive material. The device may also include a controller that is adapted to actuate the release of the particles from the release-activatable tape. In some embodiments, the controller is adapted to actuate the release of the particles from the release-activatable tape after the pressurized gas has begun to pass through the collimator.

Figure 5:
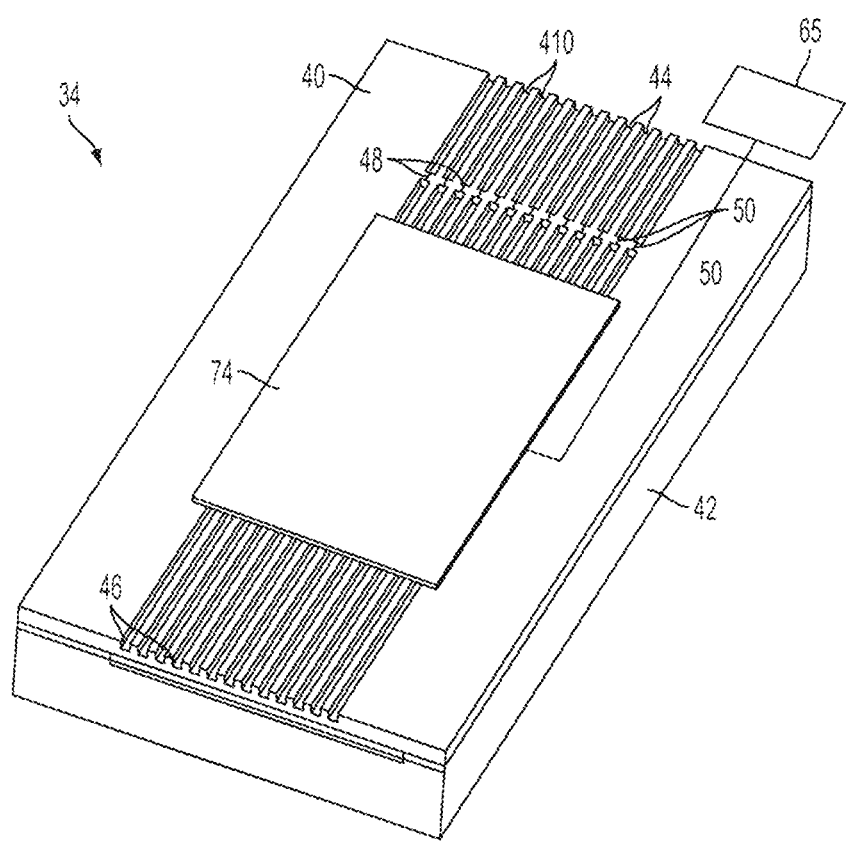
FIG. 5 illustrates an ejector for a particle delivery device and a particle-release tape in accordance with one or more embodiments of the present disclosure.

As illustrated in FIG. 5, in some embodiments, a release-activatable tape is positioned within or adjacent to the collimator 40. The particle-release tape 74 may be positioned adjacent to the conduits 410 downstream of the venturi 48 for releasing particles and entraining them in the gas stream. A controller 65 may selectively actuate the release of the particles from the particle-release tape 74.

Figure 6:
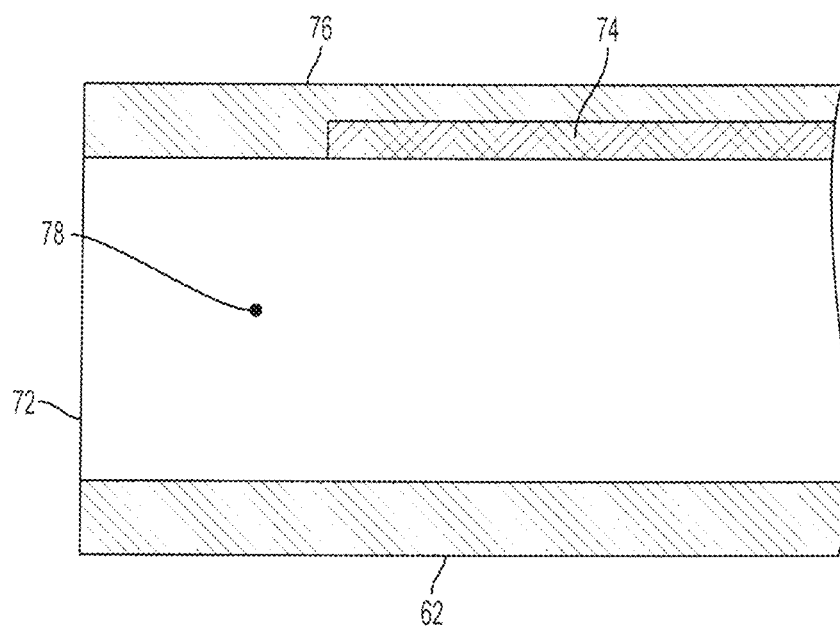
FIG. 6 shows a particle delivery device including a particle-release tape in accordance with one or more embodiments of the present disclosure.

As illustrated in FIG. 6, the particle-release tape 74 may be positioned within or adjacent to the conduits 78 of a collimator 62. In the illustrated embodiment, the particle-release tape 74 is situated within a relief that is etched, cut or milled in a surface of the collimator top plate 76. As such, the particle-release tape 74 faces the conduit 78 between the venturi and the outlet 72. When the particle-release tape 74 is actuated to release the particles contained in the particle release tape 74 (e.g., by the application of heat, UV, or electrical energy to the tape), the particles are released into the conduit 78 where they are entrained in the gas flowing through the conduit 78. Additional techniques that can be incorporated into the particle delivery devices and methods disclosed herein are described in U.S. Pat. Nos. 6,328,436, 7,188,934, and 8,550,604 which are incorporated herein by reference.

The delivery device may be configured to deliver various types of particles and may also deliver liquids, in the form of a stream or droplets. For example, the particles delivered may be or comprise heavier/denser particles that are configured to form micropores in the biological tissue; the particles delivered may be or comprise abrasive particles configured to abrade the biological tissue; the particles delivered may be or comprise lighter weight particles such as solid particles of functional material configured to interact with the biological tissue in some therapeutic or non-therapeutic way. The functional material may comprise drugs, cosmetics, nutritional or nourishing substances, tissue marking substances and/or any other types of particles. These categories of particles are not mutually exclusive and may overlap, for example, according to some implementations, the lighter weight particles may also be abrasive or the heavier/denser particles may include a coating of the functional material.

As used herein, the term "drug" refers to any chemical or biological material or compound suitable for administration by the methods previously known in the art and/or by the methods taught in the present disclosure, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anesthetic effect, or it may be systemic. The drug may be a therapeutic, prophylactic, antiangiogenic agent. For example, the drug may be a vaccine. The drug may be formulated in a substantially pure form or with one or more excipients known in the art. The excipient material may be homogenously mixed with the drug or heterogenously combined with the drug. For example, the drug may be dispersed in an excipient (matrix) material known in the art, or may be included in a core or coating layer in a multi-layered structure with an excipient material. In some embodiments, the excipient material may function to control in vivo release of the drug, for example to provide timed release (e.g., controlled or sustained release) of the drug. In some embodiments, particles may include biodegradable material that is used as a sacrificial layer/coating on the functional material and potentially for protecting the active material during jetting and penetration. In some embodiments, the biodegradable material may be a constituent for controlling the release of drug content. The heavier/denser particles may comprise biodegradable and/or dissolvable particles that are absorbed by biological tissue. Where biodegradable materials are used for the heavier particles, these approaches can reduce foreign material residence in the tissue.

Some embodiments involve the use of tissue abrasive particles in addition to the heavier/denser particles and lighter/less dense particles previously discussed. The tissue abrasive particles are suitable for abrading the surface of a biological tissue after delivery from the device and impinging the biological tissue. According to some aspects the tissue abrasive particles may be made of aluminum oxide.

The heavier/denser particles may be made of a material having density greater than 10 g/cm$^3$ and may comprise a metal such as gold, platinum or silver. The heavier/denser particles may have a shape, e.g., pointed tip, wedge shape, etc. that enhances penetrating the tissue to a predetermined depth. The heavier/denser particles are particularly effective at creating micropores in tissue.

The device may also contain and deliver nourishing or nutritional particles. The nourishing or nutritional particles may be any particles suitable for promoting or maintaining the viability of the cells of the biological tissue. Such particles may include vitamins, minerals, and other non-drug particles that contain nutrients.

The device may also contain and deliver cosmetic particles. The cosmetic particles may be any particles suitable for providing a cosmetic effect to the biological tissue when delivered to the tissue. For example, the particles may be particles that diminish the appearance of wrinkles, that provide color, such as for tattoos, or alter the coloration of the biological tissue, or that create or reduce localized swelling.

The device may also contain and deliver tissue marking particles. The tissue marking particles may be any particles suitable for marking a tissue for identification, whether such an identification may be made visually, with or without the assistance of technology (e.g., an imaging technology). For example, the particles may comprise an ink or dye or the particles may contain an agent that is visible or capable of imaging with an imaging technology, such as X-Ray, infrared (IR), magnetic resonance imaging (MRI), computed tomography (CT), or ultrasound.

In certain embodiments, the particles have a volume average diameter of about 0.1 to about 250 microns. In some embodiments, the particles have an average diameter equal to or less than ⅕ the width of the conduit or channel, and even more preferably equal to or less than 1/10 the of the width of the conduit or channel.

In some embodiments, the ejector may be configured to both collimate the particles entrained in the gas flow stream and to focus the particles. The ejector may include a focusing mechanism configured to focus the particles into a cross sectional area wherein the largest diameter of the cross sectional area is a fraction of the largest inner diameter of the conduit. In some implementations, the cross sectional area of the focused stream is less than 1/10, less than 1/100, or less than 1/1000 of the inner diameter of the conduit after focusing. In some cases, the focused, collimated stream of particles can more effectively deliver the functional material to the tissue due to spatial correlation between the first particles (heavier/denser particles) and the second particles (lighter particles of functional material). For example, the device can be configured to collimate and focus the stream of first and second particles to provide a specified spatial correlation of the particles at the impact site on the tissue. In some embodiments, the impact site of the particles has a diameter equal to or greater than the presenting cross sectional diameter of the first particles. In some embodiments, the impact site of the second particles has a diameter less than about 0.5 times the diameter of the impact site of the first particles.

When both first and second particles are ejected by the device, increased spatial correlation of these particles increases the probability that a lighter weight particle will follow a heavier weight particle into a micropore created by the heavier weight particle or that a lighter weight will be driven into the tissue by a heavier weight particle that impacts the tissue after the lighter weight particle, thereby propelling the lighter weight particle through a micropore to suitable depth in the tissue. Note that the terms "first" and "second" are used herein to identify different types of particles and are not meant to convey any particular order. The first particles may be delivered before, after, or during the time that the second particles are delivered.

Figures 7A, 7B:
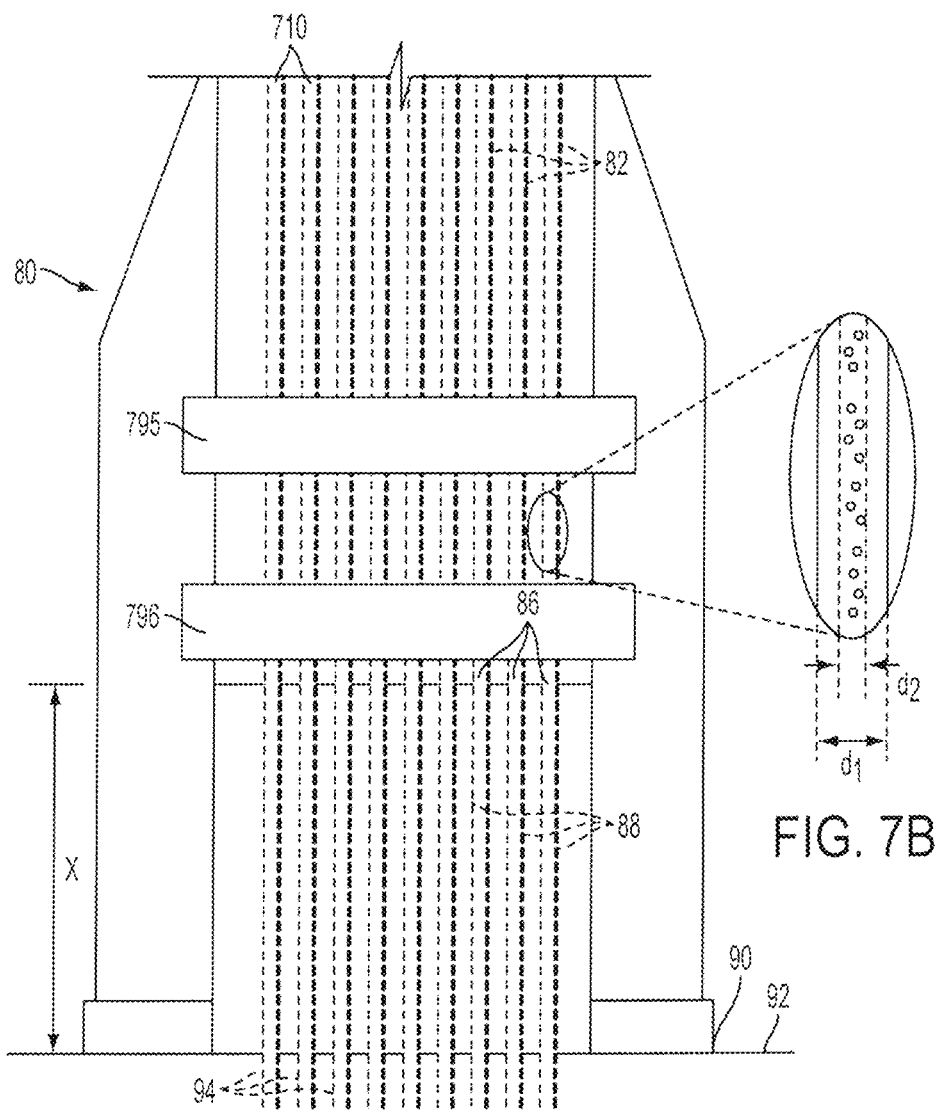
FIGS. 7A and 7B illustrate a portion of an ejector that includes a focusing mechanism configured to focus the particles into a focused beam in accordance with some embodiments.

FIG. 7A illustrates a portion of an ejector 80 including conduits 710 that form well-defined collimated streams of particles entrained in a carrier gas 88. The ejector 80 includes a focusing mechanism 795, e.g., an aerodynamic and/or electrostatic focusing mechanism, configured to focus the particles into a focused beam. A particle electrostatic accelerator 796 may optionally be used in conjunction with a particle alignment and/or particle focusing mechanism.

The particles emerge from the outlets 86 of the conduits 82 in an aligned and focused beam substantially perpendicular to the tissue surface. The ejector includes a tissue interfacing surface 90 configured to be placed on skin or other tissue. When the tissue interfacing surface 90 is placed on the skin 92, the outlets 86 are at a distance x above the surface 92. When the particles impact the skin surface 92, they may form micropores 94 in the skin.

The inset FIG. 7B shows the focused particle beam downstream of the focusing mechanism. The particle beam is focused into a cross sectional area having width $d_2$ which is a fraction, e.g., less than 1/10, less than 1/100, or less than 1/1000 of the conduit inner diameter width $d_1$ in the focus region.

Figure 8A:
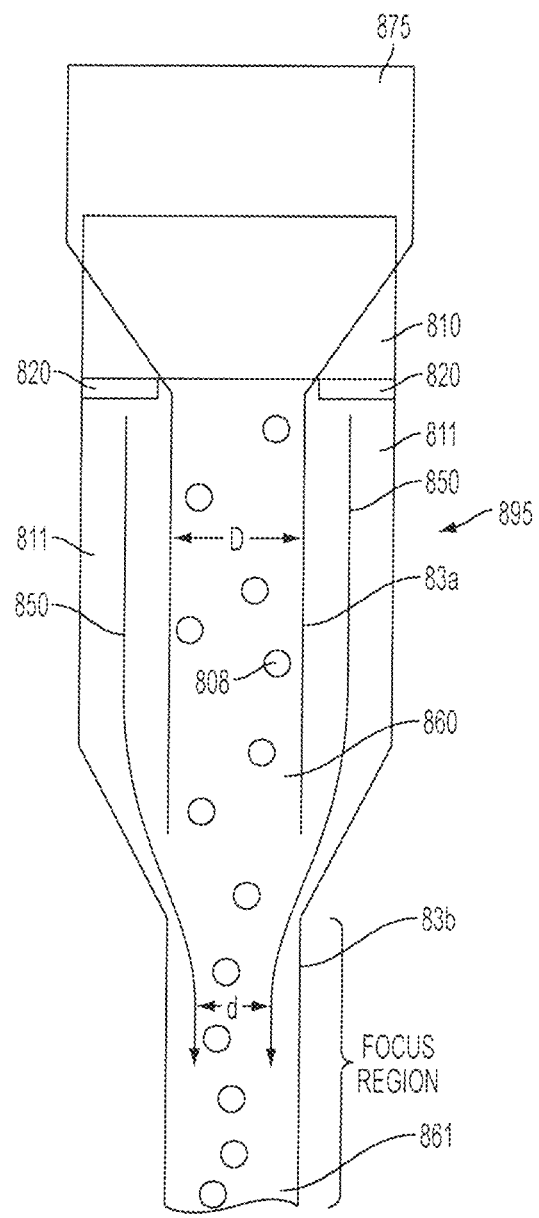
FIGS. 8A and 8B are cross sectional views of aerodynamic particle focusing mechanisms in accordance with some embodiments.

As illustrated in FIG. 8A, an aerodynamic focusing mechanism 895 may comprise at least one source 810 of sheath fluid 811 and at least one sheath fluid port 820 that allows the sheath fluid 811 to enter the conduit 83a to form at least one sheath flow stream 850 that focuses the collimated particle stream 860. In some cases, the sheath fluid may comprise the propellant used to form the collimated particle stream. In some cases, the sheath fluid may be a different from the propellant, may be or include a liquid drug, may include additional particles and/or may be a mixture of the propellant other liquid or particles. FIG. 8A illustrates the scenario wherein upstream of the focusing mechanism the conduit 83a is relatively wider and the particles are initially dispersed in the conduit. In the focus region, the sheath fluid 850 pinches the particles stream 860 in and downstream of the focus region into a particle stream 861 having a narrower cross sectional area. The largest cross sectional width of the focused particle stream is a fraction of the width of the internal diameter of the conduit in the focus region.

FIG. 8A illustrates a particle reservoir 875 configured to deliver the particles inline with the conduit 83a. The sheath 850 focuses the payload from a diameter D into a microjet of diameter d and accelerates the payload in the focus region while avoiding increases in the shear on the particle payload The flow streams in array of parallel entrainment microjet conduits and propellant gas (e.g., air, helium, etc.) may reach over 300 m/sec for 1 atm pressure input used. Much higher velocities are possible using this approach, e.g. velocities in excess of 300 m/s. Higher pressure can be used to achieve higher velocities.

Figure 8B:
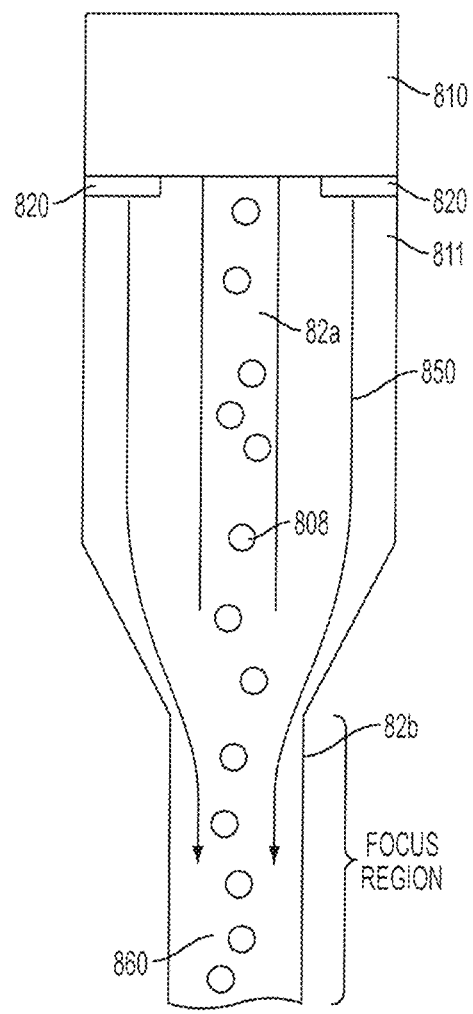

FIG. 8B illustrates the scenario wherein the conduit 82a is initially relatively narrow before the sheath fluid 811 is introduced. In the focus region, the sheath fluid 811 maintains the particle stream 860 to within a narrow cross section of the wider conduit 82b. The width of the particle stream can be actively changed/controlled by adjusting the flow rate of the gas sheath flow.

Figure 8C:
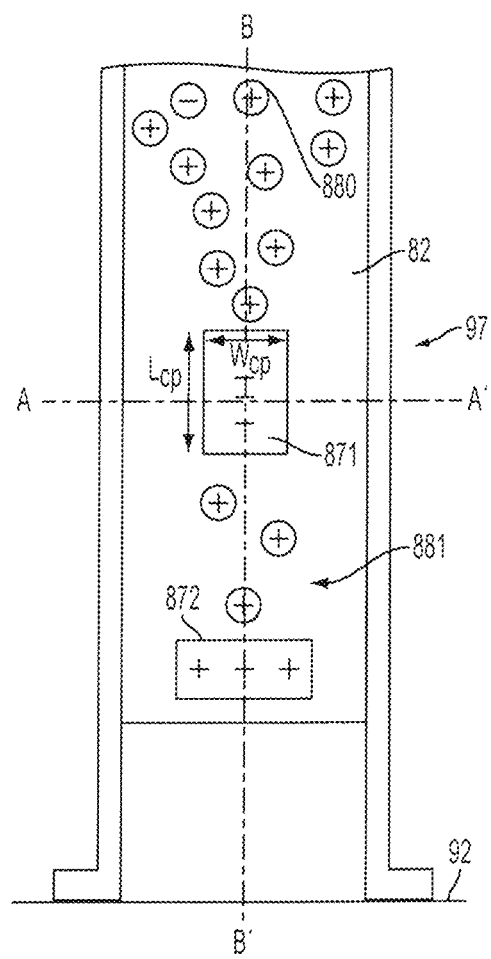
FIGS. 8C through 8E are cross sectional views of an electrostatic particle focusing mechanism in accordance with some embodiments.
Figure 8D:
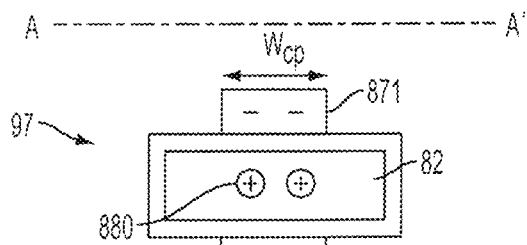
Figure 8E:
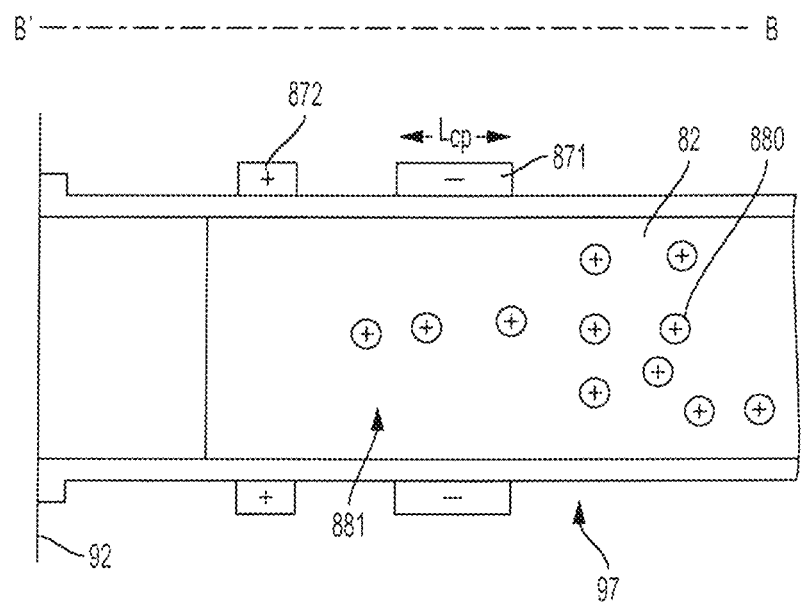
Figure 9G:
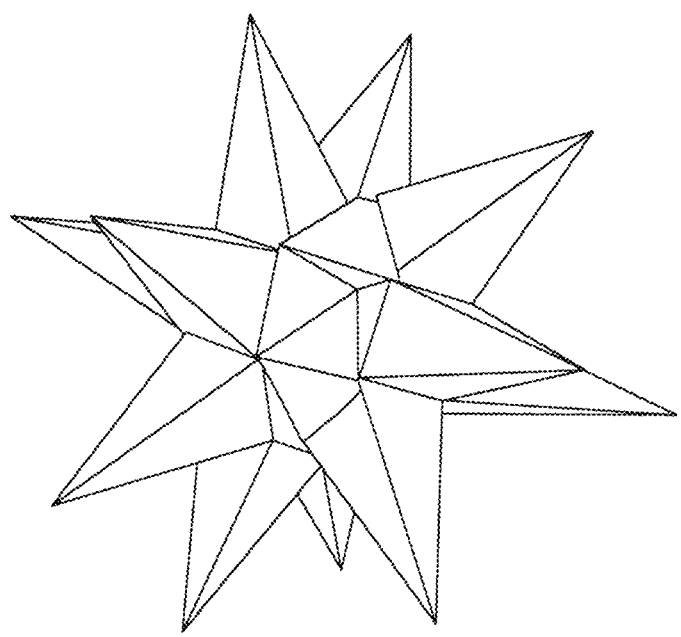
Figure 9H:
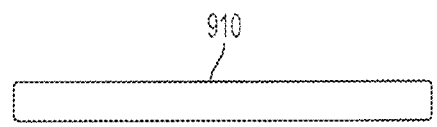
FIGS. 9H through 9L show exemplary configurations for elongated particles of functional material in accordance with various embodiments.
Figure 9I:
Figure 9J:
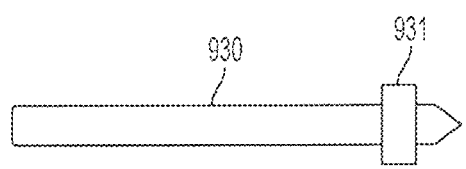
Figure 9K:
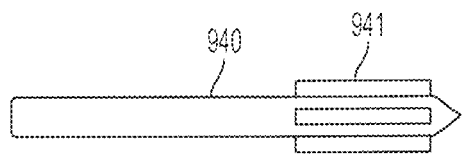
Figure 9L:
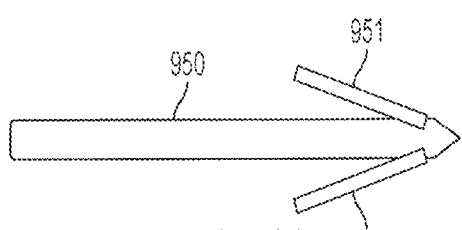
Figure 10A:
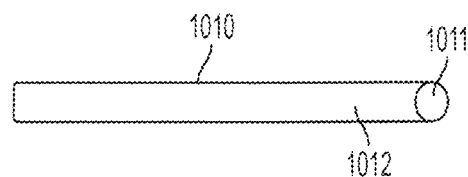
FIGS. 10A through 10C show exemplary configurations for elongated particles comprising a combination of heavier/denser material and lighter/low-density functional material in accordance with various embodiments.
Figure 10B:
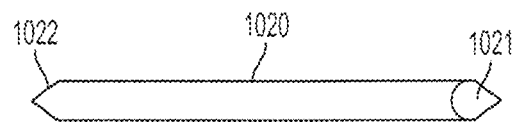
Figure 10C:
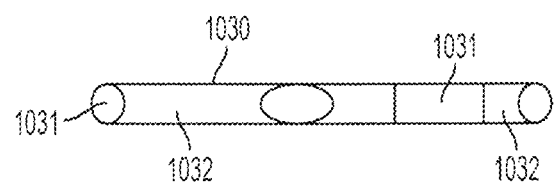
Figure 11A:
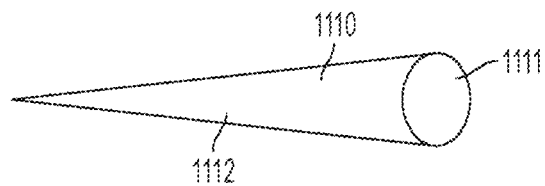
FIGS. 11A through 11D show exemplary shapes for elongated particles configured to enhance orientation control and stability according to various embodiments.
Figure 11B:
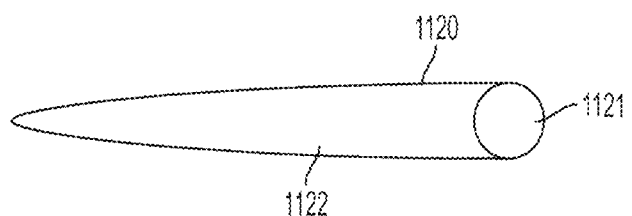
Figure 11C:
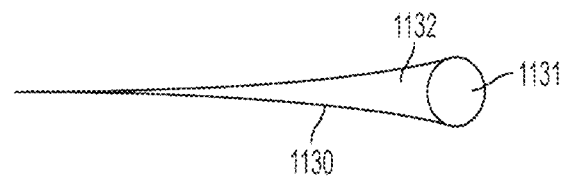
Figure 11D:
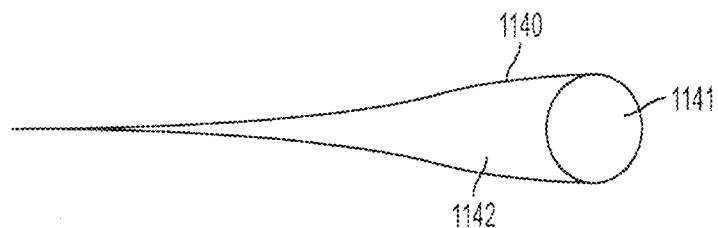

FIGS. 8C through 8E show side and end cross sectional views of an electrostatic particle focusing mechanism 97 comprising at least one charged plate 871 having a length, $L_{cp}$, and width, $W_{cp}$, that is less that the width of the conduit in the focus region and about equal to the desired focused particle beam. Particles 880 can be charged by ionization, ion bombardment, tribocharging, or other means. Particles 880 having a charge opposite the charge on the charged plate 871 are electrostatically attracted and move toward the center of the conduit 82 into a focused particle stream 881. When charged particles 880 are used, the ejector may also include an electrostatic particle accelerator as shown in FIG. 8C. The charged particles 880 are first attracted and accelerated toward the oppositely charged plate 871 and, after accelerating past the oppositely charged plate 871, are repelled by a plate 872 having the same charge as the particles 880, thus accelerating the particles 880 toward the tissue surface 92. The electrostatic focusing and/or acceleration may be used in conjunction with aerodynamic focusing using sheath fluid previously discussed.

Figure 12A:
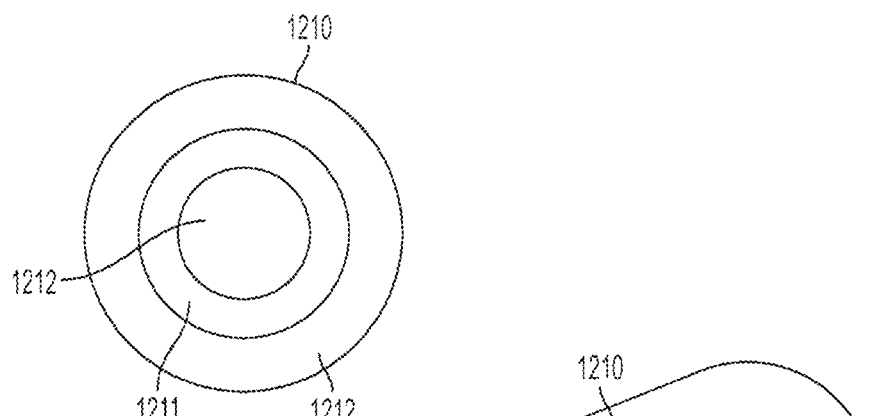
FIGS. 12A through 12C depict particles having a heavier/denser portion that has increased surface area to carry a lighter/lower density functional material in accordance with embodiments disclosed herein.
Figure 12B:
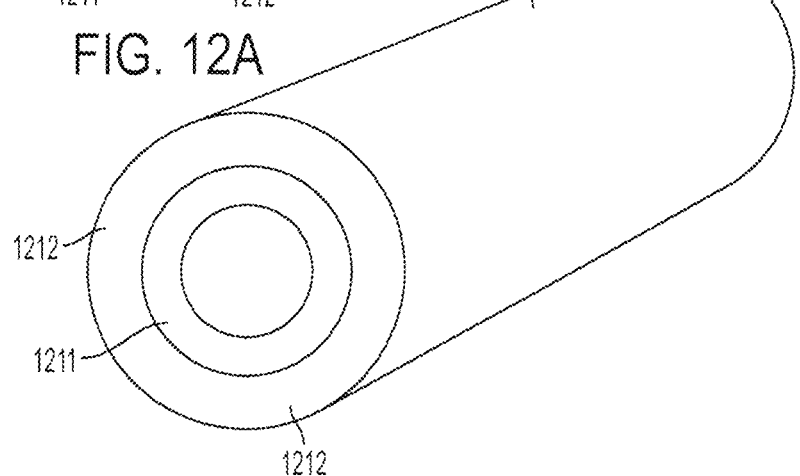

The particles delivered by the delivery device may have a variety of two dimensional and three dimensional shapes comprising lighter, functional material, e.g., drug material, and heavier/denser material, e.g., mechanoporation material. In some implementations, portions of the particles may be the lighter material and other portions may be the heavier denser material. For example, the particles may be circular or spherical as previously shown and in general have any two dimensional or three dimensional shape. Illustrative particle shapes include a star shape with any number of points, as shown in FIGS. 9A through 9F and a three dimensional star shown in FIG. 9G. The particles of FIGS. 9A through 9G may be made partially of functional material and partially of heavier denser material. In some implementations, the center or core portion of the particles may be or comprise the lighter, functional material and the elongations extending from the core may be or comprise the heavier, denser material.

According to some implementations at least some of the particles delivered by the delivery device are elongated particles, e.g., having an aspect ratio greater than about 5, or in a range of about 5 to about 50, for example. The length of the elongated particles may be in the range of about 1 μm to about 1000 μm, or in a range of about 10 μm to about 100 μm. The width of the elongated particles may be in the range of about 0.25 μm to about 100 μm, or about 2 μm to about 50 μm. In some implementations, the length and/or width of the particles may be greater than 100 μm. As discussed above, a focused, collimated particle stream may be used to enable tight spatial correlation between high density mechanoporation particles and low density drug particles. The correlation should allow a drug or other functional material to diffuse into cells before the membrane has reclosed. The use of elongated particles may be employed to further facilitate correlated delivery of heavier mechanoporation particles and lighter particles of a functional material, e.g. drug particles. A high aspect ratio and alignment of particles normal to skin surface can allow sufficiently high momentum and sufficiently small cross section for adequate penetration of drug material. The high aspect ratio scales the ratio of mass to impact cross sectional area in a beneficial manner relative to spherical form factor and enhances penetration through reduced drag.

According to some implementations, the elongated particles comprise high aspect ratio solid rods of a lighter weight, functional material, e.g., drug material, as shown in FIGS. 9H-9L. FIG. 9H shows a rod-shaped solid functional particle 910 having a high aspect ratio. FIG. 9I shows a particle 920 that is similar to that of FIG. 9H, but includes intentionally tapered ends 921 to enhance tissue penetration.

Elongated objects will align parallel to the stream lines in the conduit with maximum drag end downstream as they are accelerated by the faster moving fluid. However, because of the small drag forces in gas, the alignment time is fairly long (e.g., on the order of tens of seconds for particles in the 1 to 10 μm size range). In some configurations, even after the particles are aligned in the gas stream, small perturbations can misalign the objects again. One way to speed up the alignment and to stabilize the orientation of the particles is to add fins at one end of the elongated particles. These fins increase the drag at one end, which increases the rate of rotation into the aligned position, while stabilizing the dart against misalignments due to perturbations. As shown in FIGS. 9J and 9K, the elongated particles 930, 940 are shown with two possible implementations of the fins 931, 941. Fin 931 comprises a widened end section at one end of particle 930. Fin 941 comprises ridges at one end of particle 940. However, in some cases, protrusions can be detrimental to skin penetration. FIG. 9L illustrates fins 951 that can be broken off easily as the particle 950 enters the skin or are flimsy enough to fold back. Brush structures occur in the extracellular matrix and are easily endocytosed.

In some implementations, the elongated particles are combination particles that include a combination of materials, such as dual material, high aspect ratio structures that include a denser/heavier material in one or more regions and include a less dense, lighter weight, functional material in one or more relatively long regions of functional material.

FIGS. 10A through 10C show dual material particles 1010, 1020, 1030, e.g., comprising a high density penetration enhancer material and low density drug material). FIG. 10A shows a high density particle or material portion 1011 bonded to a relatively long functional particle or material portion 1012. For stiff formulations of the functional material it should not matter which end impacts the skin first because it is the momentum and cross section which determine the penetration depth.

The use of high aspect ratio particles increases the likelihood that particles are aligned such that they are substantially perpendicular to the tissue upon impact. One or both ends of the combination particle could be tapered to further enhance penetration, as illustrated by particle 1020 of FIG. 10B which includes a tapered heavier/denser portion 1021 on one end and a tapered functional portion 1022 on the opposing end of the high aspect ratio particle. The particle 1030 shown in FIG. 10C illustrates that multiple regions of various types of materials (e.g., heavier/denser material 1031 and lighter material 1032) can be aggregated in a linear particle configuration to adjust the total mass needed for optimal penetration and/or alignment stability. As shown in FIG. 10C, the higher weight portions 1031 of a particle (and higher weight particles in general) can have high aspect ratio shapes.

Shaping the particles can be beneficial for orientation control and stability. A few examples of shaped particles are illustrated in FIGS. 11A through 11D although it will be appreciated that there are a great number of shapes that could be used. FIGS. 11A through 11D provide an exemplary, non-limiting set of shapes, including a combination material particle 1110 comprising a heavier material 1111 and a lighter material 1112 arranged in an approximately triangular shape (FIG. 11A); a blunt tapered combination particle 1120 comprising a heavier material 1121 and a lighter material 1122 (FIG. 11B); a pointed taper combination particle 1130 comprising a heavier material 1131 and a lighter material 1132 (FIG. 11C); and a tear drop shaped combination particle 1140 (a combination of the blunt taper and pointed shapes) comprising a heavier material 1141 and a lighter material 1142.

For combination particles, the particle may be formed in shapes that increase the surface area of a heavier material that is available to carry the functional material. For example, an increase in surface area can be achieved by using a higher density material 1211 formed in a hollow shape, e.g., a hollow cylinder, as shown in the cross section (FIG. 12A) and perspective (FIG. 12B) views of particle 1210. The functional material 1212 is disposed in and on the hollow cylinder of heavier/denser material 1211.

Figure 12C:
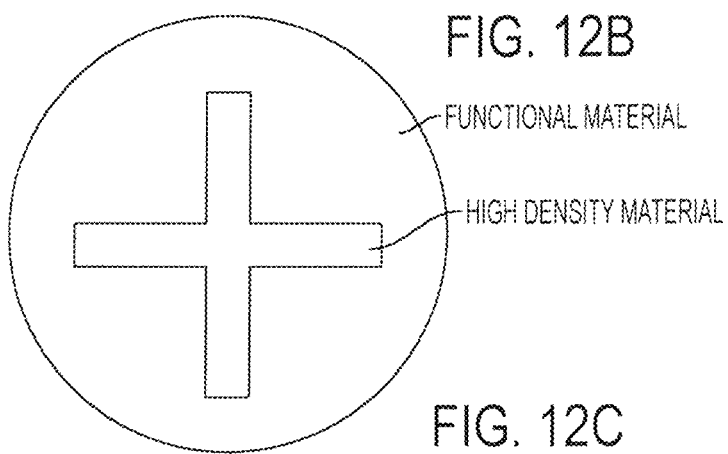

As another example, the surface of the heavier/denser material can be structured to include fins (shown in FIG. 12C) or other structured shapes (ridges, pyramids, hemispheres, etc.) that increase the surface area available to carry the functional material. The structured surface can be an inner surface, e.g., inner surface of a cylinder, an outer surface, or both the inner and outer surfaces can be structured to increase surface area. The combination particles having one or more structured surfaces may be elongated or non-elongated, e.g. a spherical particle of the heavier/denser material can have a structured surface.

The elongated particles discussed above may be used with or without focusing, however, focusing as discussed herein is particularly useful to constrain the heavier mechanoporation particles and lighter functional particles, e.g., drug particles, more tightly to increase spatial correlation significantly. In implementations that use separate heavy and light particles, either the heavy particles, the light particles, or both may be elongated.

Some embodiments involve a particle delivery device comprising a broad area ejector, such as an ejector having a few larger conduits or a single larger conduit. In some examples, the few conduits or single conduit may have an inner diameter of about 1 cm. Such a broad area ejector may be configured to deliver aligned elongated particles, such as the particles illustrated in FIGS. 9H through 9L with or without focusing. For example, in both broad area and narrow area particle ejectors, high aspect ratio particles having enhanced aerodynamic drag at the front end and/or having a higher density tail end may be aligned during acceleration of the particles as the air is flowing significantly faster than the high aspect ratio particles.

Figures 13A, 13B, 13C:
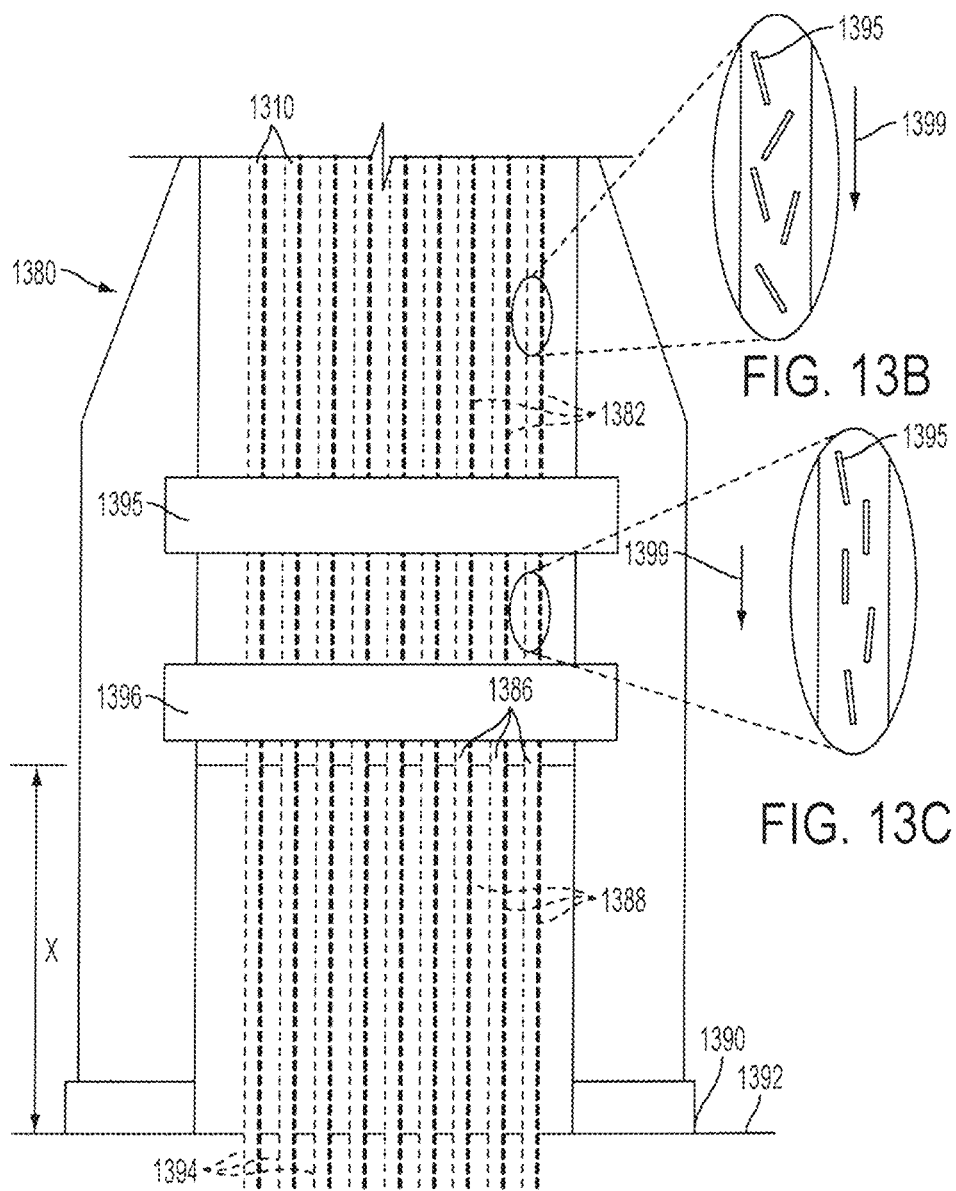
FIGS. 13A through 13C illustrate a portion of an ejector including an alignment mechanism configure to align elongated particles in accordance with various embodiments.

FIG. 13A illustrates a portion of an ejector 1380 including conduits 1310 that form well-defined collimated streams of elongated particles 1395 entrained in a carrier gas 1388. The ejector 1380 includes an alignment mechanism 1395, e.g., an aerodynamic, electrostatic, and/or magnetic alignment mechanism, configured to align the elongated particles 1395 so that the longitudinal dimension of the elongated particles is aligned with the flow direction of the gas and particle stream. For example, the elongated particles may be aligned such that the length axis of the particle makes an angle less than about 20 degrees with the flow direction 1399. A particle electrostatic accelerator 1396 may optionally be used in conjunction with the particle alignment mechanism. The ejector may also include a particle focusing mechanism in some implementations.

As shown in inset FIG. 13B, upstream from the particle alignment mechanism 1395, the elongated particles 1395 may be non-aligned with respect to the direction of flow 1399. Non-aligned means that the length axes of most of the particles are oriented at angles greater than ±20 degrees with respect to the flow direction.

After the particles interact with the alignment mechanism 1395, the elongated particles 1395 are substantially aligned, e.g., the length axis of a substantial majority (greater than 75%) the particles makes an angle of less than about ±20 degrees or even ±5 degrees with respect to the flow direction 1399 as illustrated in the inset FIG. 13C. The two mechanisms of alignment due to differential shearing and torque due to mass distribution during acceleration may tend to align ends with higher drag and lower mass toward tissue end of flow.

The ejector 1380 includes a tissue interfacing surface 1390 configured to be placed on skin or other tissue 1392. When the tissue interfacing surface 1390 is placed on or near the skin 1392, the conduit outlets 1386 are at a distance x (see FIG. 13A) above the surface 1392. In some implementations, the tissue interfacing surface 1390 may be a component of a structure, such as a hollow flexible tube. When the particles 1395 impact the skin surface 1392, they form micropores 1394 in the skin and the carrier gas 1388 travels substantially parallel to the skin 1392.

Figure 14:
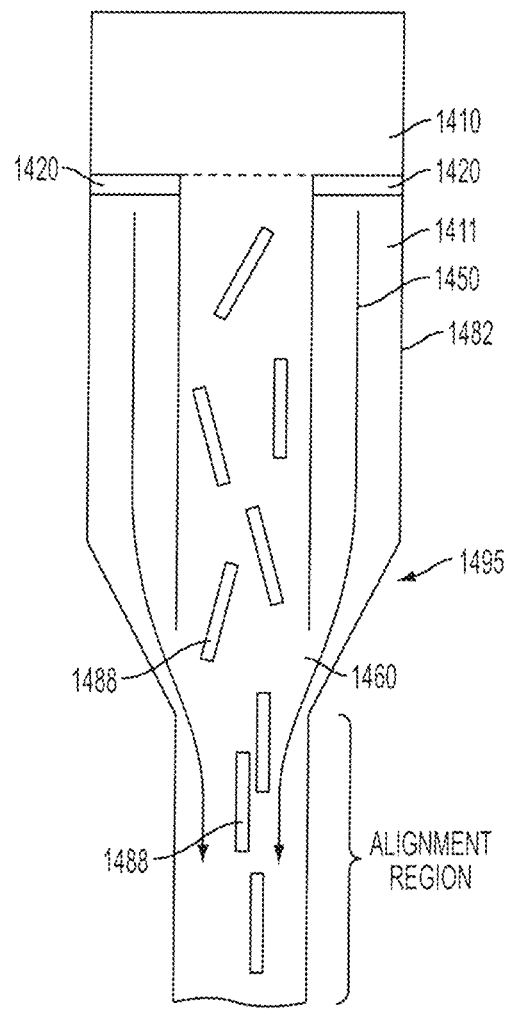
FIG. 14 is a cross sectional view of an aerodynamic particle alignment mechanism in accordance with one or more embodiments.

As illustrated in FIG. 14, an aerodynamic alignment mechanism 1495 may comprise, for example, at least one source 1410 of sheath fluid 1411 and at least one sheath fluid port 1420 that allows the sheath fluid 1411 to enter the conduit 1482 to form at least one sheath flow stream 1450 that aligns the elongated particles 1488 in the collimated particle stream 1460. As shown in FIG. 14, before interaction with the sheath fluid 1411, the particles 1488 are less aligned than the particles 1488 downstream in the alignment region. The sheath fluid may comprise the propellant used to form the collimated particle stream. In some cases, the sheath fluid may be a different from the propellant, and may be or include a liquid drug, a gas, and/or a liquid or gas that contains additional solid particles. As illustrated by the example of FIG. 14, a stream of propellant gas and particles several microns in diameter can be injected into a laminar sheath flow of air. The particle ejector may be designed to reduce turbulence which can be accomplished for low Reynolds numbers at such small scales. Diffusion between the propellant and sheath flows is negligible in the time from ejection into the sheath and impact with the tissue. Thus lateral spatial correlation can be enhanced in rough proportion to the ratio of the diameter of the full conduit and the carrier stream. Arbitrary loading of first (heavier/denser) material and the drug or other functional material can be chosen to provide sufficient drug delivery.

Figure 15A:
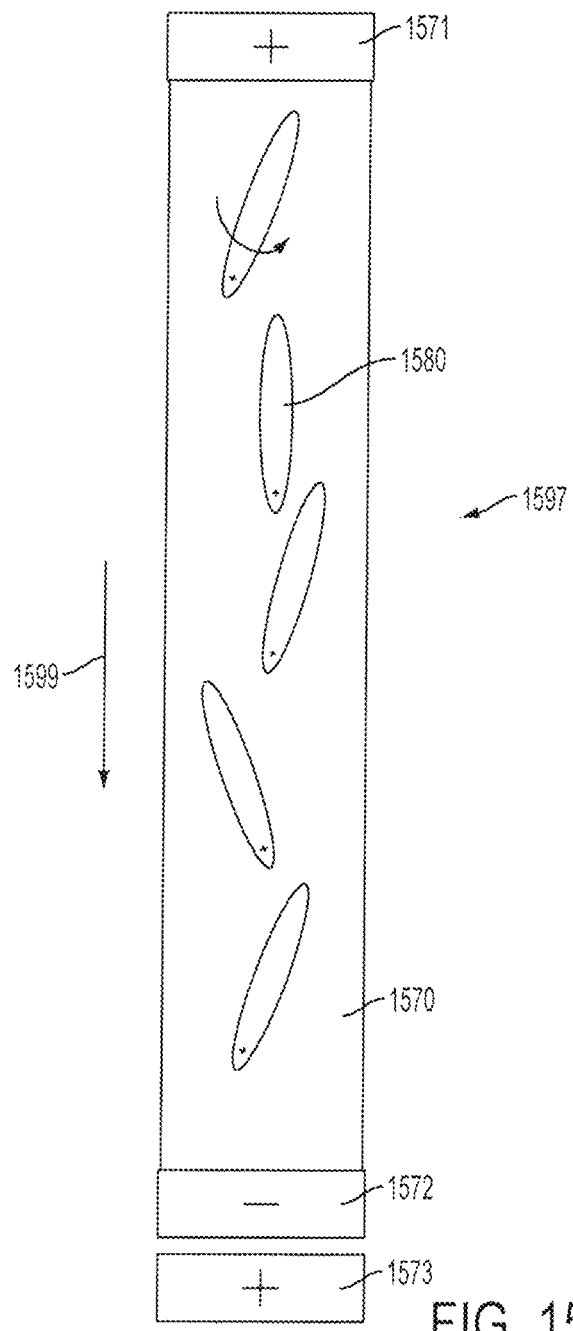
FIG. 15A is a cross sectional view of an electrostatic particle alignment mechanism and particle accelerator in accordance with one or more embodiments.

FIG. 15A shows an electrostatic particle alignment mechanism 1597 comprising one or more charged plates 1571, 1572 disposed proximate to the conduit 1570. As illustrated in FIG. 15, the electrostatically charged plates 1571 1572 comprise a positively charged plate 1571 and a negatively charged plate 1572 spaced apart from one another and wrapped around the conduit 1570. Particles 1580 moving along direction 1599 are positively charged at one end causing the charged end to be repelled from and rotate away from the positively charged plate 1571 and to be attracted to and rotate toward the negatively charged plate 1572 thus causing rotational alignment of the particles 1580 in the conduit 1570.

When charged particles 1580 are delivered, charged plates 1571, 1572, 1573 may be used as an electrostatic particle accelerator. The charged particles 1580 are first repelled by plate 1571 and are accelerated toward the oppositely charged plate 1572. After accelerating past the oppositely charged plate 1572, the positively charged particles 1580 are repelled by a plate 1573 which has the same charge as the particles, thus accelerating the particles 1580 toward the tissue surface. With charge at only one end of the high aspect ratio particles electric fields can be used to retard one end and effectively enhance the aerodynamic alignment effectiveness of the air which is moving at a higher speed than the particles.

Figure 15B:
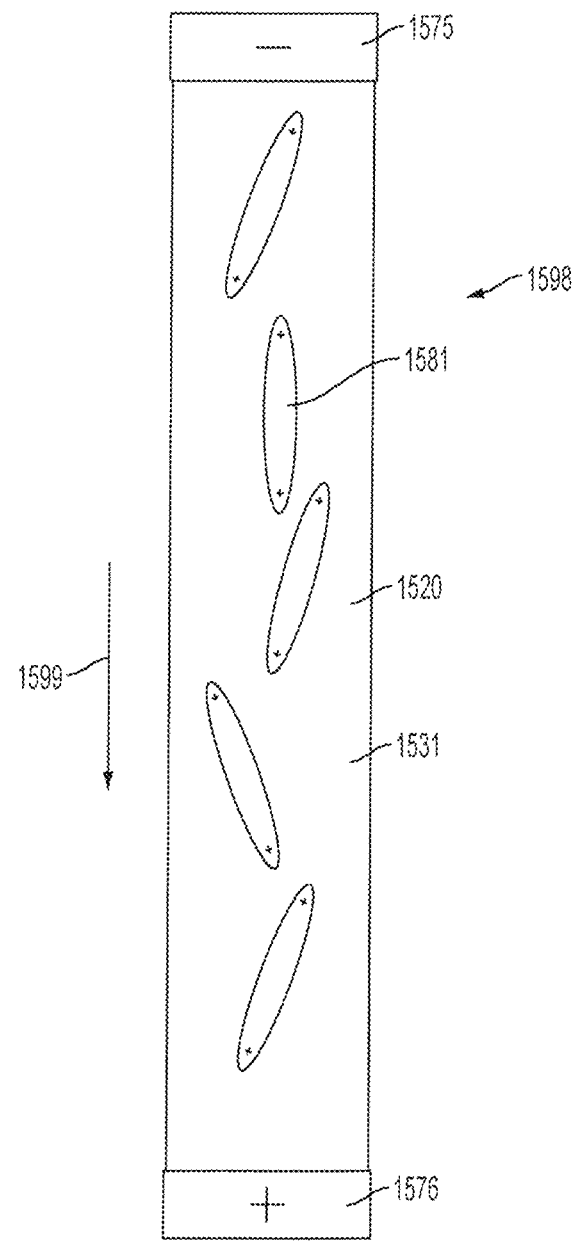
FIG. 15B is a cross sectional view of an electrostatic particle alignment mechanism in accordance with one or more embodiments.

Another configuration of an alignment mechanism 1598 is shown in FIG. 15B. Particles 1581 are oppositely charged at either end forming a dipole and are entrained in the gas propellant 1520 as they move through conduit 1531 along direction 1599. The charged plates 1575, 1576 create an axial field which provides an aligning torque to the dipolar particles.

Figure 16A:
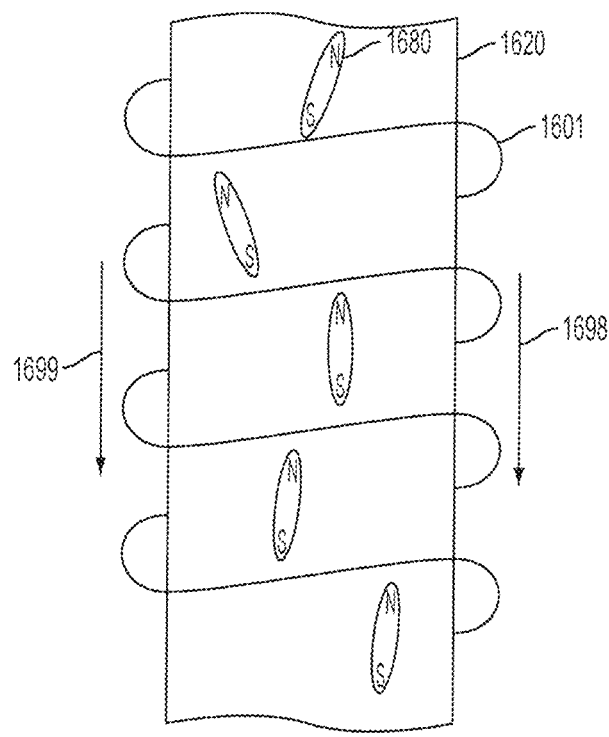
FIG. 16A is a cross sectional view of a magnetic particle alignment mechanism in accordance with one or more embodiments.
Figure 16B:
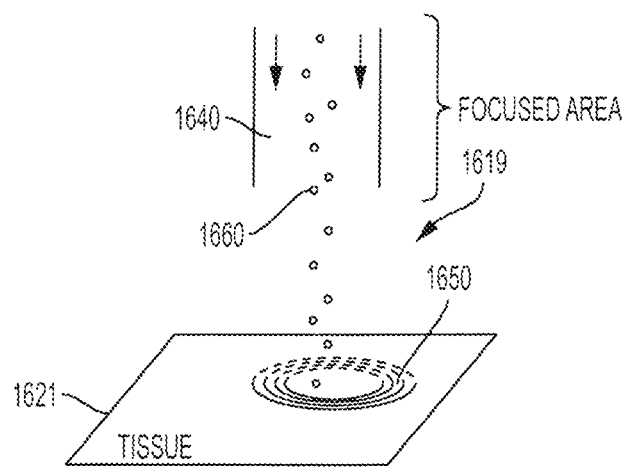
FIG. 16B is a cross sectional view of a portion of a particle delivery device that includes a particle accelerator in accordance with some embodiments.
Figure 16C:
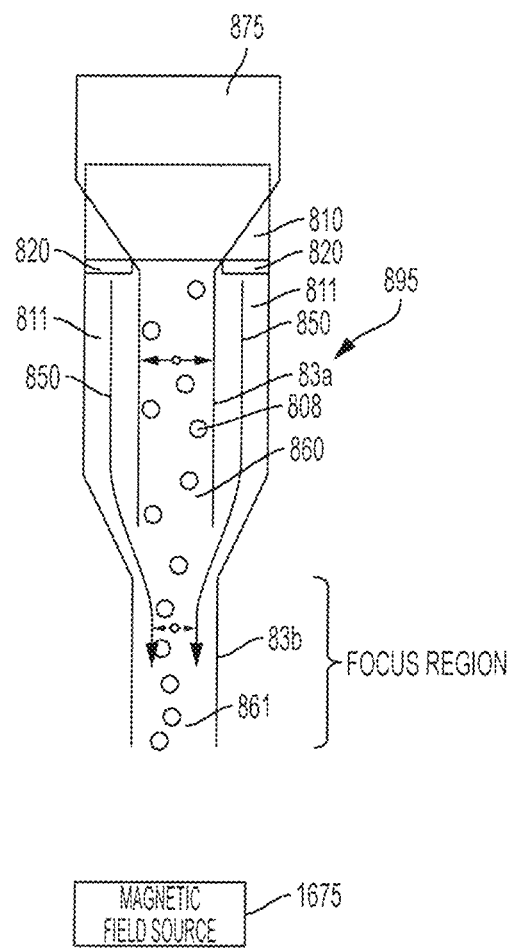
FIG. 16C is a cross sectional view of a portion of a particle delivery device that includes a particle accelerator in accordance with some embodiments.
Figure 16D:
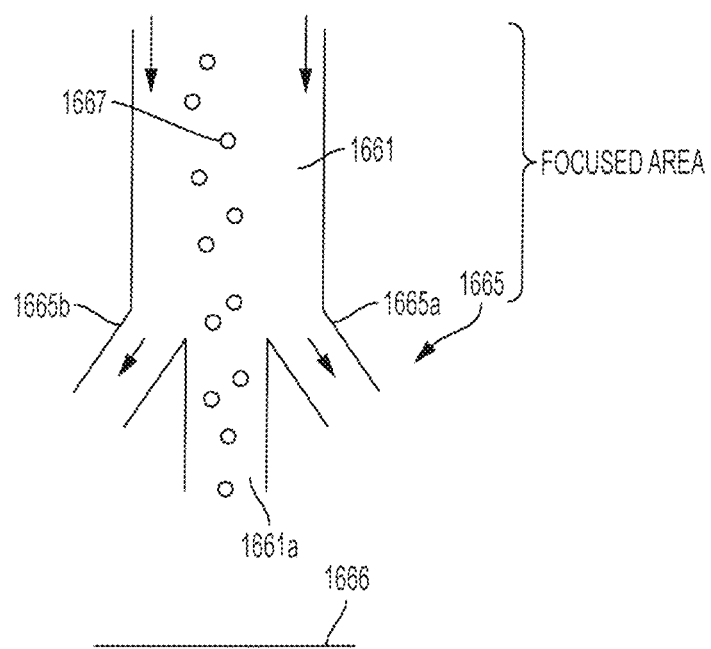
FIG. 16D is a cross sectional view of a portion of a particle delivery device that includes a mechanism to decelerate the focusing stream in accordance with some embodiments.
Figure 17:
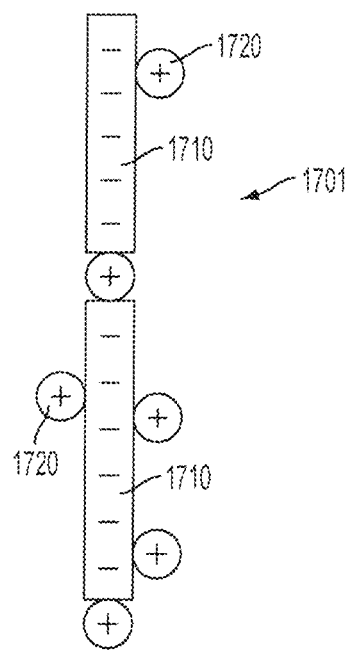
FIG. 17 illustrates an agglomeration of charged particles in accordance with some embodiments.
Figure 18:
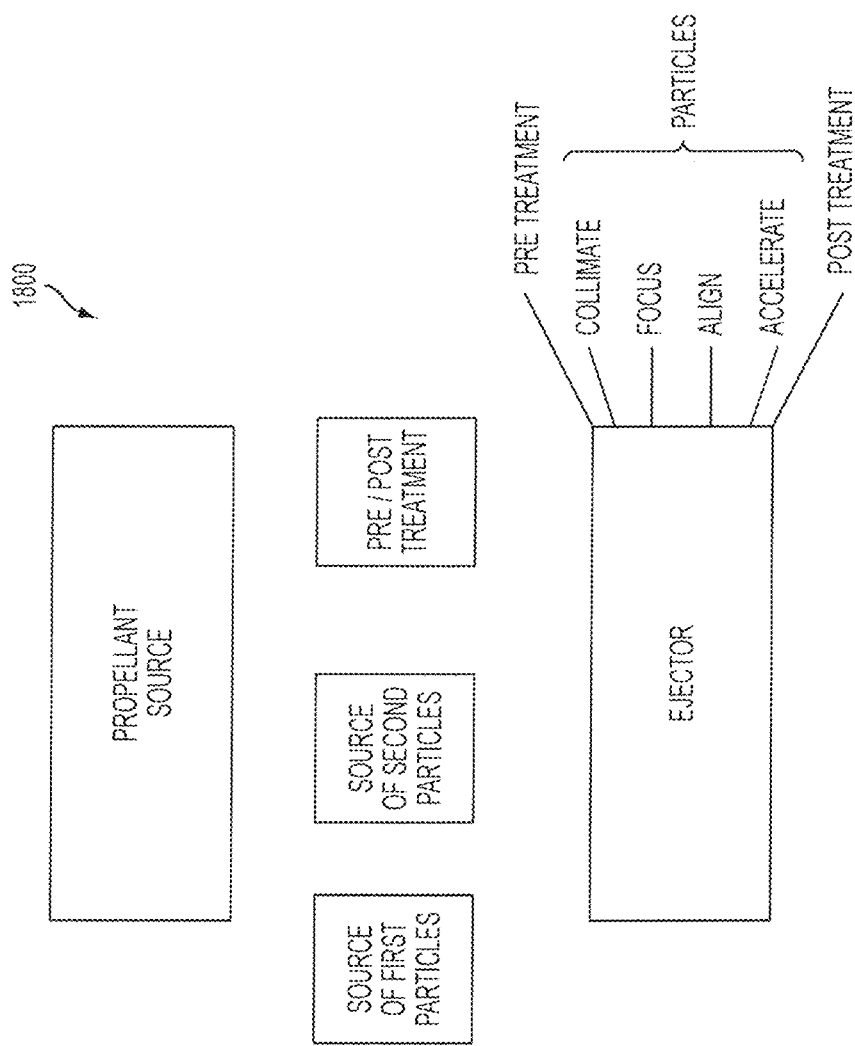
FIG. 18 is a block diagram of a particle delivery device in accordance with various embodiments.

FIG. 16A illustrates a magnetic alignment mechanism for a particle delivery device. Magnetic, elongated particles 1680 move through the conduit 1620 generally along direction 1699. A solenoid 1601 is coaxial with the conduit 1620 and generates a magnetic field having direction 1698. The magnetic field operates on magnetic particles 1680 causing magnetic particles 1680 to align with the field.

In some embodiments, a magnetic field gradient is used to focus the particles and to accelerate the magnetic particles toward the tissue The magnetic particle focusing and acceleration mechanism may be used, for example, in conjunction with the magnetic particle alignment mechanism of FIG. 16A and/or may be used with any of the particle focusing approaches disclosed herein. As shown in FIG. 16B, the particle focus accelerator 1619 may comprise a planar electromagnetic coil 1650 located near the tissue 1621. When activated, the planar coil 1650 generates a gradient magnetic field that focuses and accelerates magnetic particles 1660 moving in the channel 1640 toward the tissue 1621. The diameter of the planar coil 1650 controls the focusing of the particle stream and the strength of the magnetic field, which is controlled by the current through the coil 1650, controls the particle acceleration.

FIG. 16C illustrates a magnetic particle accelerator comprising a magnetic field source 1675, such as the planar coil 1675 previously discussed located downstream from the particle focusing mechanism shown in FIG. 8A. The magnetic field source 1675 creates a gradient magnetic field that accelerates magnetic particles toward the tissue. According to some implementations, the first particles may be accelerated, e.g., electrostatically or magnetically, accelerated whereas the second particles are not electrostatically or magnetically accelerated causing the first particles to attain a higher velocity than the velocity of the second particles.

In some configurations it can be helpful to remove and/or decelerate at least some of the propellant in the high speed stream of particles just before or just after the focused particle stream is unconstrained by the channel. FIG. 16D illustrates a propellant deceleration mechanism 1665 located near the outlet 1661*a* of the conduit 1661 near tissue 1666. The deceleration mechanism includes channels 1665*a*, 1665*b* that remove some of the propellant and allow the focused particle stream 1667 to continue to proceed toward the conduit outlet 1661*a*. In some implementations, the channels 1665*a, b* may be coupled to a vacuum source. Deceleration/redirection of the propellant serves to reduce splash back of the propellant and particles and/or reduces the damage to the tissue.

In some implementations, charged particles can be used to increase spatial correlation of heavier/denser particles and lighter functional particles as shown in FIG. 17. the first particles 1710 (heavier/denser particles) are charged and the second particles 1720 (functional lighter particles) are oppositely charged. The first particles 1720 are repelled by each other as are the second particles 1710. However, the first and second particles 1710, 1720 are attracted to each other. The attraction between the first and second particles 1710, 1720 enhances spatial correlation of the first and second particles as particles of opposite charge sign form particle agglomerations 1701 as depicted in FIG. 17. Agglomerating particles in this way may also serve to enhance penetration of the particles into the tissue.

In some embodiments, the delivery device is capable of delivering a treatment to the tissue before and/or after delivery of the particles that enhances absorption of the functional material. For example, in some implementations, the pretreatment may involve bombarding the tissue with abrasive particles, delivering a liquid drug or other liquid to the tissue, forming micropores in and/or abrading the tissue surface using a laser, applying electromagnetic pulses to the tissue.

FIG. 18 is a block diagram of a particle delivery device 1800 in accordance with some configurations discussed herein. The particle delivery device 1800 includes one or more ejectors comprising conduits, a propellant source fluidically coupled to the conduits, and sources for first and second particles, each source coupled to openings in the conduit walls for introduction of the first and/or second particles into the conduits. One or both of the first and second particles may be elongated, charged and/or magnetized particles. Each ejector includes at least one conduit into which the propellant is released, forming gas streams that entrain the first (heavier/denser) particles and/or second (lighter, functional) particles as they are introduced into the conduits. The ejectors are configured to collimate, focus, align, and/or accelerate the first and/or second particles as the particles move through the conduits. Optionally, the delivery device 1800 includes one or more pre or post treatment substance or apparatus. Optionally, the delivery device 1800 includes a unit or structure for redirecting the sheath gas at the conduit outlet leaving the particles traveling at high speed to impinge on the tissue. The pre or post treatment substance may comprise a particle, a liquid, or a gas. The pre/post treatment particle/liquid/gas may be delivered to the tissue through the conduits, with the pre/post treatment substance entering the conduits through openings in the conduit walls.

In some implementations, the pre/post treatment apparatus is an energy source that delivers energy to the tissue. In various implementations, the energy source may provide optical energy, high frequency electromagnetic energy, and/or ultrasonic energy, for example.

In one implementation, the pre/post treatment apparatus comprises an edge emitting semiconductor laser arranged such that the laser light generated by the laser (or array of lasers) travels through and is guided in each conduit to the tissue surface. The laser light may abrade the tissue surface before and/or after delivery of the first and/or second particles in some cases. In a higher power implementation, the laser light may have sufficient energy to produce micropores in the tissue to a depth suitable for delivering the functional substance, e.g., at a depth range of about 1 μm to about 1 mm. A lens or other focusing element may be located at the output end of the delivery device to provide for focusing the laser light into a high power spot on the skin to provide microporation.

In some implementations, the pre/post treatment apparatus may comprise a generator configured to produce magnetic pulses that enhance skin/mucosal surface permeation and provide for enhanced absorption of the functional material (dermaporation for skin delivery). For example, the generator can be configured to generate magnetic fields having a peak magnetic field of 5 mT, pulse duration of 400 μs, and duty cycle of 5% or an average magnetic field of 0.25 mT or more.

In some implementations, the pre/post treatment apparatus may comprise a generator configured to produce electrical pulses that provide electroporation for enhanced absorption of the functional material. For example, the generator can be configured to apply 50 V transdermally in 200 ms pulses or 100 V in 1 ms pulses. In some implementations, the pre/post treatment apparatus may comprise an ultrasonic generator configured to generate ultrasonic waves that increase the permeability of tissue.

Some embodiments discussed herein provide for physical tissue permeation enhancement to enable uptake of solid drug powder or other functional substances. These techniques increase cell wall permeation for subsequent payload penetration, through mechanoporation via particles. A delivery device discussed herein uses multiple conduits that can provide an array of precision spot target zones and enables multiparticle delivery schemes. In some implementations, all the conduits are used to eject particles and in other implementations fewer than all of the conduits are used to eject the particles. For example, the conduits of the delivery device may be sourced with particles or not in a gray scale manner to create patterned implantation of functional particles. Heavy/dense inert particles can be jetted into the tissue, forming transient diffusion pathways and enhancing cell wall permeability in a mechanoporation step that occurs before, simultaneous with or after delivery of the functional material to the tissue. The highly loaded, lighter mass drug particulates can be jetted to reach the target spot for internalization by cells. The approaches discussed herein may utilize micro electrical mechanical systems (MEMS) arrayed channels that provide confined jet streams and high probabilities for target overlap for the two types of particles. An in-line parallel device design confines particles to a few streamlines (to less than a few particle diameters in width) in the center of the conduit thus creating high probabilities for particles being well aligned, spatially correlated with one another. This width can be maintained when the particle stream is unconstrained by the conduit walls and reaches the tissue surface as previously discussed.

To realize drug internalization by cells, the drug should be interstitially transported to the mechanoporated regions. Since this architecture provides micro-scale spatial precision to accurately land the drug particles in <10-20 μm proximity to the mechanoporated cells, the diffusion time for interstitial transport of pDNA (<400 s; considering the interstitial diffusion coefficient, D, is ~$10^{-8}$ to $5\times10^{-9}$ cm$^2$/s) scales with the duration of the cell wall recovery times (~9 min for pore resealing using other methods).

In some scenarios, cell wall recovery times can be very slow compared to the particle arrival frequency and therefore, the light solid particles arrival times to the target site and transport times into the cell can be faster than cell wall recovery times and thus pDNA will be able to internalize by cells. The approaches discussed herein can enable significantly higher doses and efficiencies than technologies that are restricted to low concentration coated payloads for intracellular delivery (low density solid drug particles delivered by these devices do not penetrate deep and do not enter cells). The individual delivery spots on the tissue can be smaller (e.g., less than 50 μm) and massively arrayed with low cost MEMS fabrication. In some cases plastic injection molding can be used for high volume manufacturing.

Figure 19A:
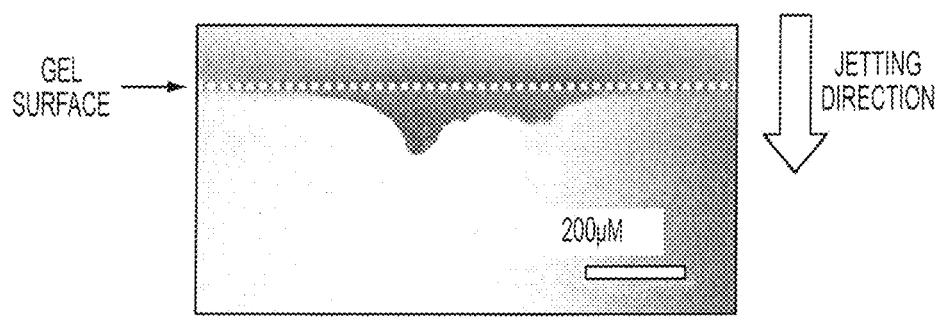
FIGS. 19A through 19C are photographs comparing mechanoporation and drug delivery using light functional particles, heavy inert particles, and both heavy inert particles and light functional particles.
Figure 19B:
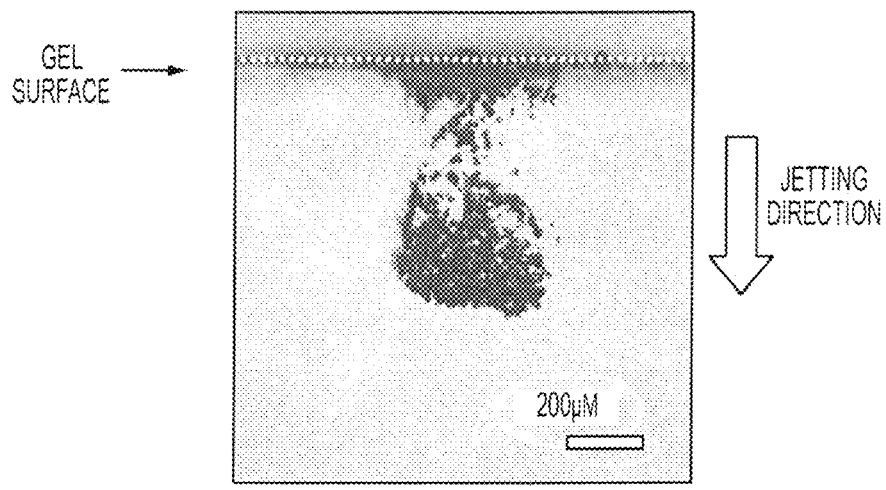
Figure 19C:
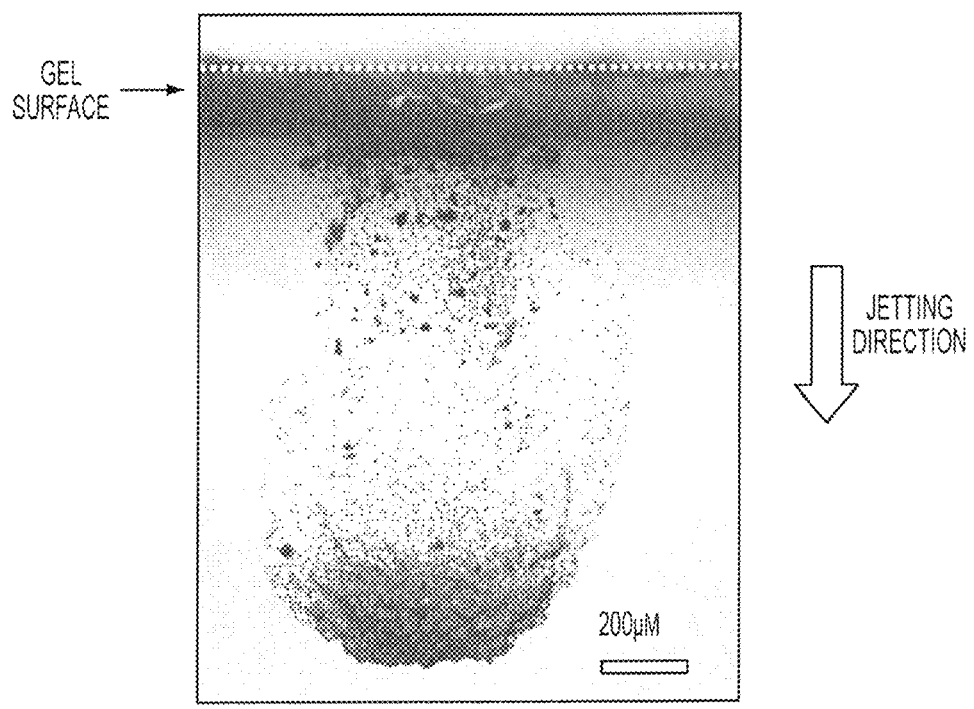

FIGS. 19A through 19C show experimentally observed penetration enhancement of a drug in a gel that simulates biological tissue. The lighter particles when used alone have good drug loading but show poor penetration as shown in FIG. 19A. The heavy/dense particles when used alone have good penetration but poor drug loading as shown in FIG. 19B. FIG. 19C shows the results for heavy particles followed by light particles. This technique exhibits almost 10× deeper penetration of lighter functional particles than when the lighter particles are used alone.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. A device for delivery of particles into biological tissue comprising:
   at least one conduit;
   a propellant source fluidically coupled to the conduit and configured to deliver a propellant into the conduit;
   a particle source configured to release magnetic elongated particles into the conduit, the elongated particles having a width, w, a length, l>w, the propellant source and the conduit configured to propel the elongated particles in a collimated particle stream toward the biological tissue;
   an alignment mechanism comprising a magnetic field generator that is configured to generate a magnetic field within the conduit and align a longitudinal axis of the magnetic elongated particles to be substantially parallel to a direction of the particle stream in an alignment region of the conduit, wherein the aligned elongated particles are ejected from the conduit and impact the biological tissue.

2. The device of claim 1, wherein the alignment mechanism comprises an aerodynamic alignment mechanism that includes:
   a source of sheath fluid; and
   one or more ports in the conduit configured to allow entry of the sheath fluid into the conduit in one or more sheath streams adjacent to the particle stream, the one or more sheath streams configured to align the longitudinal axis of the elongated particles along the direction of the particle stream in the alignment region.

3. The device of claim 1, wherein:
   the elongated particles are electrically charged; and
   the alignment mechanism comprises an electrostatic alignment mechanism comprising one or more charged plates arranged proximate to the conduit.

4. The device of claim 1, wherein the magnetic field generator comprises a solenoid coaxial with the conduit.

5. The device of claim 1, wherein the elongated particles have at least one pointed tip.

6. The device of claim 1, wherein the elongated particles have one or more fins.

7. The device of claim 6, wherein the fins are configured to break off or fold back when the elongated particles penetrate the biological tissue.

8. The device of claim 1, wherein the elongated particles are solid particles of a functional material that interacts with the biological tissue.

9. The device of claim 1, wherein the elongated particles include at least a first material and a second material, wherein the second material is a functional material that interacts with the biological tissue and the first material is a biologically inert material that has higher density than the second material.

10. The device of claim 9, wherein a volume of the second material is greater than a volume of the first material.

11. The device of claim 1, further comprising a magnetic particle accelerator comprising a magnetic field source configured to creates a gradient magnetic field that accelerates magnetic particles toward the biological tissue.

12. The device of claim 1, wherein the elongated particles comprise a drug, a cosmetic, a biologically nourishing material, or a marking material.

13. The device of claim 1, further comprising an additional particle source configured to release additional particles into the particle stream, wherein the elongated particles comprise a functional material that interacts with the biological tissue and the additional particles have a higher density than a density of the elongated particles.

14. The device of claim 13, wherein:
the elongated particles are electrostatically charged;
the additional particles are oppositely electrostatically charged; and
the elongated particles and the additional particles form particle agglomerations as the particles are transported in the particle stream.

15. A method for delivery of particles into biological tissue comprising:
releasing magnetic elongated particles into a conduit;
propelling the elongated particles in a collimated particle stream in the conduit, the elongated particles having a width, w, a length, l>w, and an aspect ratio, l/w;
magnetically aligning a longitudinal axis of the elongated particles to be substantially parallel to a direction of the collimated particle stream; and
ejecting the aligned elongated particles from the conduit toward the biological tissue.

16. The method of claim 15, wherein aligning the longitudinal axis of elongated particles comprises introducing a sheath fluid into the conduit in one or more sheath streams adjacent to the collimated particle stream, the one or more sheath streams operating to align the longitudinal axis of the elongated particles to be substantially parallel to the direction of the particle stream in an alignment region.

17. The method of claim 15, further comprising accelerating the aligned elongated particles in the particles stream toward the biological tissue using a magnetic particle accelerator.

18. The method of claim 15, wherein each of the elongated particles comprises one or more of increased density at one end of the elongated particle and an aerodynamic drag feature.

19. The method of claim 15, further comprising pre or post treating the biological tissue before or after ejecting the aligned elongated particles from the conduit toward the biological tissue.

20. The method of claim 19, wherein the pre or post treating comprises at least one of a laser treatment, a magnetic treatment, an electromagnetic treatment, an ultrasonic treatment and a chemical treatment.

* * * * *